(12) United States Patent
Chemin et al.

(10) Patent No.: US 8,715,667 B2
(45) Date of Patent: May 6, 2014

(54) METHODS OF TREATING PATIENTS HAVING TLR3-POSITIVE CANCER

(75) Inventors: Karine Chemin, Venissieux (FR); Laurent Gauthier, Marseilles (FR); Yannis Morel, Marseilles (FR); Carine Paturel, Marcy L'Etoile (FR); Agnes Tisserant, Le Puy Ste Reparade (FR)

(73) Assignee: Innate Pharma, Marseille (FR)

( * ) Notice: Subject to any disclaimer, the term of this patent is extended or adjusted under 35 U.S.C. 154(b) by 0 days.

(21) Appl. No.: 13/585,874

(22) Filed: Aug. 15, 2012

(65) Prior Publication Data

US 2012/0308581 A1 Dec. 6, 2012

Related U.S. Application Data

(62) Division of application No. 13/119,341, filed as application No. PCT/EP2009/061902 on Sep. 15, 2009, now Pat. No. 8,273,541.

(60) Provisional application No. 61/097,676, filed on Sep. 17, 2008.

(51) Int. Cl.
*A61K 39/395* (2006.01)
*A61K 48/00* (2006.01)
*A61K 38/00* (2006.01)
*G01N 33/53* (2006.01)

(52) U.S. Cl.
USPC .................... 424/143.1; 424/174.1; 514/19.3; 514/19.4; 514/44 R; 435/7.1

(58) Field of Classification Search
None
See application file for complete search history.

(56) References Cited

PUBLICATIONS

Stedman's online Medical Dictionary: Grave's Disease.*
Stedman's online Medical Dictionary: Rheumatoid Arthritis.*
Stedman's online Medical Dictionary: Diabetes Mellitus.*
Stedman's online Medical Dictionary: Appendicitis.*
Stedman's online Medical Dictionary: Multiple sclerosis.*
Salaun et al, Cancer Research 2011, vol. 71, No. 5, pp. 1-8, Jun. 2013.*
Stedman's online Medical Dictionary: Grave's Disease, 1 page; downloaded May 30, 2013.*
Stedman's online Medical Dictionary: Rheumatoid Arthritis, 1 page; downloaded May 30, 2013.*
Stedman's online Medical Dictionary: Diabetes Mellitus, 1 page; downloaded May 30, 2013.*
Stedman's online Medical Dictionary: Appendicitis, 1 page; downloaded May 30, 2013.*
Stedman's online Medical Dictionary: Multiple sclerosis, 1 page; downloaded May 30, 2013.*
Jorgenson, R. L. et al. "Human Endometrial Epithelial Cells Cyclically Express Toll-Like Receptor 3 (TLR3) and Exhibit TLR3-Dependent Responses to dsRNA" *Human Immunology*, May 1, 2005, pp. 469-482, vol. 66, No. 5.
Mozer-Lisewska, I. et al. "Tissue Localization of Toll-Like Receptors in Biopsy Specimens of Liver from Children Infected with Hepatitis C Virus" *Scandinavian Journal of Immunology*, Oct. 2005, pp. 407-412, vol. 62.
Gupta, S. M. et al. "Toll-Like Receptors and Cytokines as Surrogate Biomarkers for Evaluating Vaginal Immune Response following Microbicide Administration" *Mediators of Inflammation Journal*, 2008, pp. 1-11, vol. 2008.
Matsumoto, M. et al. "Establishment of a monoclonal antibody against human Toll-like receptor 3 that blocks double-stranded RNA-mediated signaling" *Biochemical and Biophysical Research Communications*, 2002, pp. 1364-1369, vol. 239, No. 5.

* cited by examiner

*Primary Examiner* — Bridget E Bunner
*Assistant Examiner* — Fozia Hamud
(74) *Attorney, Agent, or Firm* — Saliwanchik, Lloyd & Eisenschenk

(57) ABSTRACT

The present invention relates to antibodies, antibody fragments, and derivatives thereof that specifically bind to TLR3 cell receptors present on the surface of cells. The invention also relates to hybridomas producing such antibodies; methods of making such antibodies; fragments, variants, and derivatives of the antibodies; pharmaceutical compositions comprising the same; methods of using the antibodies to detect TLR3 levels on the surface of cells, and the use of such antibodies and compositions for diagnostic or therapeutic purposes in subjects.

10 Claims, 1 Drawing Sheet

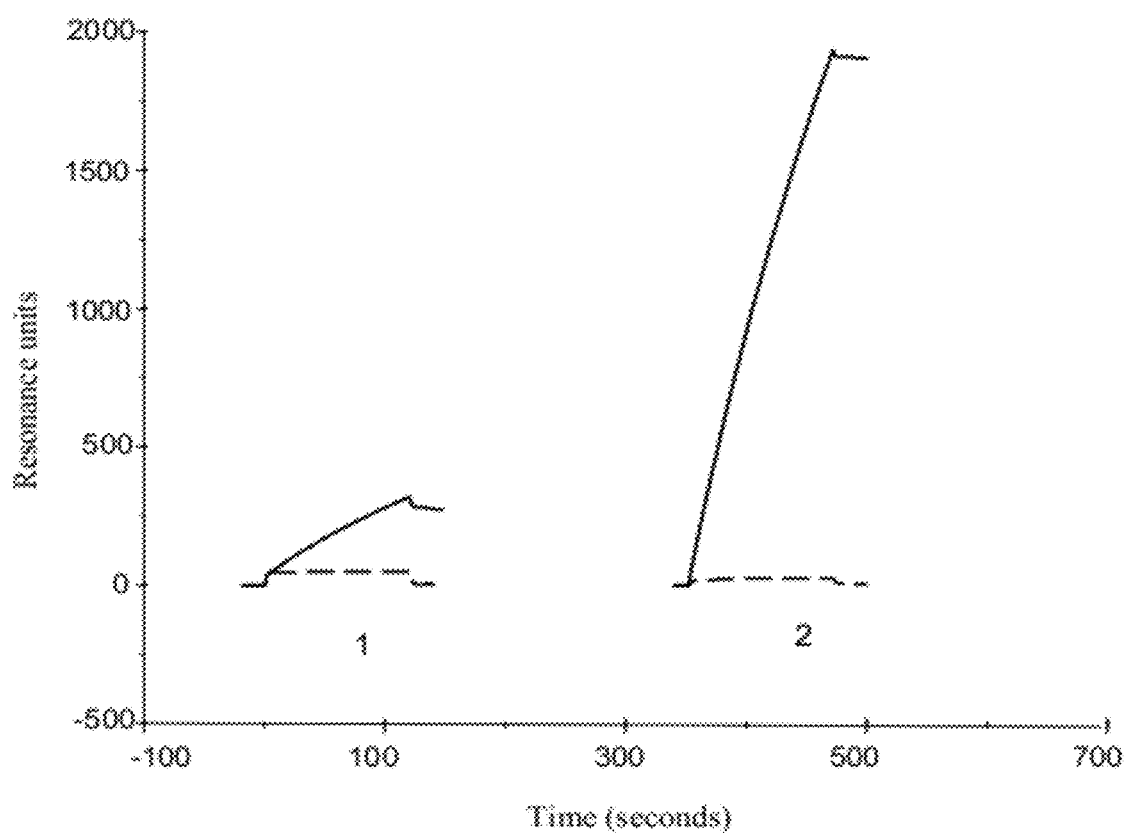

SEQUENCE LISTING

```
<160> NUMBER OF SEQ ID NOS: 11

<210> SEQ ID NO 1
<211> LENGTH: 904
<212> TYPE: PRT
<213> ORGANISM: Homo sapiens

<400> SEQUENCE: 1

Met Arg Gln Thr Leu Pro Cys Ile Tyr Phe Trp Gly Gly Leu Leu Pro
1               5                  10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240
```

-continued

```
Leu Cys Leu Glu Leu Ala Asn Thr Ser Ile Arg Asn Leu Ser Leu Ser
                245                 250                 255
Asn Ser Gln Leu Ser Thr Thr Ser Asn Thr Thr Phe Leu Gly Leu Lys
            260                 265                 270
Trp Thr Asn Leu Thr Met Leu Asp Leu Ser Tyr Asn Asn Leu Asn Val
        275                 280                 285
Val Gly Asn Asp Ser Phe Ala Trp Leu Pro Gln Leu Glu Tyr Phe Phe
    290                 295                 300
Leu Glu Tyr Asn Asn Ile Gln His Leu Phe Ser His Ser Leu His Gly
305                 310                 315                 320
Leu Phe Asn Val Arg Tyr Leu Asn Leu Lys Arg Ser Phe Thr Lys Gln
                325                 330                 335
Ser Ile Ser Leu Ala Ser Leu Pro Lys Ile Asp Asp Phe Ser Phe Gln
            340                 345                 350
Trp Leu Lys Cys Leu Glu His Leu Asn Met Glu Asp Asn Asp Ile Pro
        355                 360                 365
Gly Ile Lys Ser Asn Met Phe Thr Gly Leu Ile Asn Leu Lys Tyr Leu
    370                 375                 380
Ser Leu Ser Asn Ser Phe Thr Ser Leu Arg Thr Leu Thr Asn Glu Thr
385                 390                 395                 400
Phe Val Ser Leu Ala His Ser Pro Leu His Ile Leu Asn Leu Thr Lys
                405                 410                 415
Asn Lys Ile Ser Lys Ile Glu Ser Asp Ala Phe Ser Trp Leu Gly His
            420                 425                 430
Leu Glu Val Leu Asp Leu Gly Leu Asn Glu Ile Gly Gln Glu Leu Thr
        435                 440                 445
Gly Gln Glu Trp Arg Gly Leu Glu Asn Ile Phe Glu Ile Tyr Leu Ser
    450                 455                 460
Tyr Asn Lys Tyr Leu Gln Leu Thr Arg Asn Ser Phe Ala Leu Val Pro
465                 470                 475                 480
Ser Leu Gln Arg Leu Met Leu Arg Arg Val Ala Leu Lys Asn Val Asp
                485                 490                 495
Ser Ser Pro Ser Pro Phe Gln Pro Leu Arg Asn Leu Thr Ile Leu Asp
            500                 505                 510
Leu Ser Asn Asn Asn Ile Ala Asn Ile Asn Asp Asp Met Leu Glu Gly
        515                 520                 525
Leu Glu Lys Leu Glu Ile Leu Asp Leu Gln His Asn Asn Leu Ala Arg
    530                 535                 540
Leu Trp Lys His Ala Asn Pro Gly Gly Pro Ile Tyr Phe Leu Lys Gly
545                 550                 555                 560
Leu Ser His Leu His Ile Leu Asn Leu Glu Ser Asn Gly Phe Asp Glu
                565                 570                 575
Ile Pro Val Glu Val Phe Lys Asp Leu Phe Glu Leu Lys Ile Ile Asp
            580                 585                 590
Leu Gly Leu Asn Asn Leu Asn Thr Leu Pro Ala Ser Val Phe Asn Asn
        595                 600                 605
Gln Val Ser Leu Lys Ser Leu Asn Leu Gln Lys Asn Leu Ile Thr Ser
    610                 615                 620
Val Glu Lys Lys Val Phe Gly Pro Ala Phe Arg Asn Leu Thr Glu Leu
625                 630                 635                 640
Asp Met Arg Phe Asn Pro Phe Asp Cys Thr Cys Glu Ser Ile Ala Trp
                645                 650                 655
Phe Val Asn Trp Ile Asn Glu Thr His Thr Asn Ile Pro Glu Leu Ser
            660                 665                 670
```

```
Ser His Tyr Leu Cys Asn Thr Pro His Tyr His Gly Phe Pro Val
            675                 680                 685

Arg Leu Phe Asp Thr Ser Ser Cys Lys Asp Ser Ala Pro Phe Glu Leu
690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
            725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
            770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
            805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
            835                 840                 845

Leu Val Phe Leu Glu Glu Ile Pro Asp Tyr Lys Leu Asn His Ala Leu
            850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
            885                 890                 895

Leu Gly Ser Lys Asn Ser Val His
            900

<210> SEQ ID NO 2
<211> LENGTH: 839
<212> TYPE: PRT
<213> ORGANISM: Homo sapiens

<400> SEQUENCE: 2

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
        50                  55                  60

Pro Leu Arg His Leu Gly Ser Tyr Ser Phe Ser Phe Pro Glu Leu
65                  70                  75                  80

Gln Val Leu Asp Leu Ser Arg Cys Glu Ile Gln Thr Ile Glu Asp Gly
            85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
130                 135                 140
```

```
Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
            165                 170                 175

Leu Glu His Leu Asp Leu Ser Ser Asn Lys Ile Gln Ser Ile Tyr Cys
        180                 185                 190

Thr Asp Leu Arg Val Leu His Gln Met Pro Leu Leu Asn Leu Ser Leu
            195                 200                 205

Asp Leu Ser Leu Asn Pro Met Asn Phe Ile Gln Pro Gly Ala Phe Lys
        210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
        355                 360                 365

Glu Val Asp Leu Pro Ser Leu Glu Phe Leu Asp Leu Ser Arg Asn Gly
        370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
        435                 440                 445

Leu Ile Tyr Leu Asp Ile Ser His Thr His Thr Arg Val Ala Phe Asn
450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
        515                 520                 525

His Asn Asn Phe Phe Ser Leu Asp Thr Phe Pro Tyr Lys Cys Leu Asn
        530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
```

```
                    565                 570                 575
Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835

<210> SEQ ID NO 3
<211> LENGTH: 113
<212> TYPE: PRT
<213> ORGANISM: Mus musculus
<220> FEATURE:
<221> NAME/KEY: DOMAIN
<222> LOCATION: (24)..(39)
<223> OTHER INFORMATION: CDR1
<220> FEATURE:
<221> NAME/KEY: DOMAIN
<222> LOCATION: (55)..(61)
<223> OTHER INFORMATION: CDR2
<220> FEATURE:
<221> NAME/KEY: DOMAIN
<222> LOCATION: (94)..(102)
<223> OTHER INFORMATION: CDR3

<400> SEQUENCE: 3

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
```

```
                35                  40                  45
Pro Lys Arg Leu Ile Tyr Leu Val Ser Lys Leu Asp Ser Gly Val Pro
            50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ile His Leu Pro Tyr Thr Phe Gly Gly Gly Thr Lys Leu Glu Ile Lys
            100                 105                 110
Arg

<210> SEQ ID NO 4
<211> LENGTH: 113
<212> TYPE: PRT
<213> ORGANISM: Mus musculus
<220> FEATURE:
<221> NAME/KEY: DOMAIN
<222> LOCATION: (27)..(35)
<223> OTHER INFORMATION: CDR1
<220> FEATURE:
<221> NAME/KEY: DOMAIN
<222> LOCATION: (52)..(66)
<223> OTHER INFORMATION: CDR2
<220> FEATURE:
<221> NAME/KEY: DOMAIN
<222> LOCATION: (99)..(103)
<223> OTHER INFORMATION: CDR3

<400> SEQUENCE: 4

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Ala Asn Thr Gly Glu Pro Thr Tyr Ala Glu Glu Phe
    50                  55                  60

Lys Gly Arg Phe Ala Phe Ser Leu Glu Thr Ser Asp Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Asp Tyr Asp Tyr Trp Gly Gln Gly Thr Thr Leu Thr Val Ser
            100                 105                 110
Ser

<210> SEQ ID NO 5
<211> LENGTH: 16
<212> TYPE: PRT
<213> ORGANISM: Mus musculus

<400> SEQUENCE: 5

Lys Ser Ser Gln Ser Leu Leu Asp Ser Asp Gly Lys Thr Tyr Leu Asn
1               5                   10                  15

<210> SEQ ID NO 6
<211> LENGTH: 7
<212> TYPE: PRT
<213> ORGANISM: Mus musculus

<400> SEQUENCE: 6

Leu Val Ser Lys Leu Asp Ser
1               5
```

```
<210> SEQ ID NO 7
<211> LENGTH: 9
<212> TYPE: PRT
<213> ORGANISM: Mus musculus

<400> SEQUENCE: 7

Trp Gln Gly Ile His Leu Pro Tyr Thr
1               5

<210> SEQ ID NO 8
<211> LENGTH: 9
<212> TYPE: PRT
<213> ORGANISM: Mus musculus

<400> SEQUENCE: 8

Tyr Thr Phe Thr Asn Tyr Gly Met Asn
1               5

<210> SEQ ID NO 9
<211> LENGTH: 15
<212> TYPE: PRT
<213> ORGANISM: Mus musculus

<400> SEQUENCE: 9

Asn Ala Asn Thr Gly Glu Pro Thr Tyr Ala Glu Glu Phe Lys Gly
1               5                   10                  15

<210> SEQ ID NO 10
<211> LENGTH: 4
<212> TYPE: PRT
<213> ORGANISM: Mus musculus

<400> SEQUENCE: 10

Asp Tyr Asp Tyr
1

<210> SEQ ID NO 11
<211> LENGTH: 13
<212> TYPE: PRT
<213> ORGANISM: Mus musculus

<400> SEQUENCE: 11

Lys Ala Ser Gly Tyr Thr Phe Thr Asn Tyr Gly Met Asn
1               5                   10
```

METHODS OF TREATING PATIENTS HAVING TLR3-POSITIVE CANCER

CROSS-REFERENCE TO RELATED APPLICATIONS

This application is a divisional of U.S. Ser. No. 13/119,341, filed May 11, 2011, now U.S. Pat. No. 8,273,541, which is the U.S. national stage application of International Patent Application No. PCT/EP2009/061902, filed Sep. 15, 2009, which claims the benefit of U.S. Provisional Patent Application No. 61/097,676, filed Sep. 17, 2008, the disclosures of which are hereby incorporated by reference in their entireties, including all figures, tables and amino acid or nucleic acid sequences.

The Sequence Listing for this application is labeled "Seq-List.txt" which was created on Mar. 11, 2011 and is 19 KB. The entire contents of the sequence listing is incorporated herein by reference in its entirety.

FIELD OF THE INVENTION

The present invention relates to antibodies, antibody fragments, and derivatives thereof that specifically bind to TLR3 cell receptors present on the surface of cells. The invention also relates to hybridomas producing such antibodies; methods of making such antibodies; fragments, variants, and derivatives of the antibodies; pharmaceutical compositions comprising the same; methods of using the antibodies to detect TLR3 levels on the surface of cells, and the use of such antibodies and compositions for diagnostic or therapeutic purposes in subjects.

BACKGROUND

Cancer is a major cause of death in the world. Because traditional cancer therapy targets all rapidly dividing cells, these therapies can have devastating side effects because they affect non-cancerous cells such as cells of the gastrointestinal tract, immune system, and hair follicles. Therefore, new methods of treatment are needed that are able to more specifically target cancer cells and, as such, avoid the side effects typical of cancer therapy.

*Drosophila* toll proteins control dorsal-ventral patterning and are thought to represent an ancient host defense mechanism. In humans, TLRs are believed to be an important component of innate immunity. Human and *Drosophila* Toll protein sequences show homology over the entire length of the protein chains. The family of human Toll-like receptors is comprised of ten highly conserved receptor proteins, TLR1-TLR10. Like *Drosophila* toll, human TLRs are type I transmembrane proteins with an extracellular domain consisting of a leucine-rich repeat (LRR) domain that recognizes pathogen-associated molecular patterns (PAMPs), and a cytoplasmic domain that is homologous to the cytoplasmic domain of the human interleukin-1 (IL-1) receptor. Similar to the signaling pathways for both *Drosophila* toll and the IL-1 receptor, human Toll-like receptors signal through the NF-κB pathway.

Although the different mammalian TLRs share many characteristics and signal transduction mechanisms, their biological functions are very different. This is due in part to the fact that four different adaptor molecules (MyD88, TIRAP, TRIF and TRAF) are associated in various combinations with the TLRs and mediate different signaling pathways. In addition, different ligands for one TLR may preferentially activate different signal transduction pathways. Furthermore, the TLRs are differentially expressed in various hematopoietic and non-hematopoietic cells. Accordingly, the response to a TLR ligand depends not only on the signal pathway activated by the TLR, but also on the nature of the cells in which the individual TLR is expressed.

Although ligands for some TLRs remain to be identified, a number of TLR specific ligands have been reported. For example, TLR3 ligands (agonists) include double stranded RNA such as Poly IC and Poly AU. Polyinosinic-polycytidylic acid (Poly IC) is a high molecular weight synthetic double stranded RNA that is heterogeneous in size. Polyadenylic-polyuridylic acid (Poly AU) is a double stranded complex of synthetic polyribonucleotides. Both Poly IC and Poly AU have been used in several clinical trials as adjuvant therapy in different types of cancer, such as cancer of the breast, bladder, kidney and stomach.

Stimulation of TLR3 by double stranded RNA or other agonists in, e.g., dendritic cells or B lymphocytes leads to the production of cytokines such as IFN, the activation of the innate immune system (NK cells), the enhancement of CD8+ T cells, and antigen cross-priming by dendritic cells. Accordingly, TLR3 plays an important role in the defense against viral infection, and agonists have been used as adjuvants for cancer therapy in the past (see, e.g., Lacour et al. (1980) *Lancet* 2: 161-164; Khan et al., (1995) *Eur. J. Surg. Oncol.* 21:224-227).

While most studies of human TLRs, e.g., TLR3, have focused on their role in immune cells, it is now clear that they are also widely expressed in non-immune cells, including transformed cells such as breast cancer, cervical cancer, hepatomas, and melanomas, among others. Indeed, there is evidence that the efficacy of TLR3 agonists such as poly-AU or poly-IC in cancer therapy is not necessarily based on immune cell activation but on the induction of apoptosis in TLR3-expressing tumor cells (see, e.g., Salaun et al. Clin Cancer Res (2007); 4565 13(15) Aug. 1, 2007; Salaun et al., 2006, The Journal of Immunology, 176: 4894-4901; the entire disclosures of which are herein incorporated by reference). Because such TLR3 agonist therapy depends on the expression of TLR3 in the tumor cells, therefore, it is of obvious utility to be able to reliably and easily detect TLR3 levels in tumor cells.

A simple and practical way of detecting the expression of specific proteins in vivo is by immunostaining of paraffin-embedded tissue sections. Using this method, thin sections of tissue (e.g., cancer tissue obtained by biopsy) are obtained, fixed in e.g., formalin, embedded in paraffin, and then cut into very thin sections and mounted on slides. Following deparaffination, the slides are amenable to, e.g., immunohistochemical methods to detect the expression of specific proteins. This method is particularly useful because it gives rise to stable preparations in which the specific cellular and intracellular localization of specific proteins can be assessed.

Unfortunately, however, it is not always possible to find antibodies, particularly monoclonal antibodies, that work effectively and specifically in paraffin-embedded sections. Indeed, it is often much more difficult to obtain useful antibodies for immunohistochemistry on paraffin-embedded slides than it is for antibodies for use in other detection methods such as immunoblotting. The present invention addresses these and other needs.

SUMMARY OF THE INVENTION

The present invention provides novel compositions and methods involving antibodies, antibody fragments, and derivatives that allow specific binding to human TLR3-expressing cells, particularly in paraffin-embedded sections.

Such compositions and methods are useful for a multitude of applications, particularly for detecting TLR3 expression and expression levels in cells or tissues, e.g., prior to TLR3-agonist therapy. In addition, antibodies of the invention can be used for purifying TLR3-expressing cells, for stimulating or inhibiting TLR receptors and for specifically labeling TLR3-expressing cells in vitro or in vivo, e.g. for diagnostic or therapeutic purposes.

Accordingly, in one aspect, the present invention provides a monoclonal antibody that specifically binds a human TLR3 polypeptide, wherein said antibody specifically binds to said TLR3 polypeptide in paraffin-embedded tissue sections. In one embodiment of the invention, the antibody competes for binding to the same TLR3 epitope as monoclonal antibody 40F9. In another embodiment, the antibody is a mouse antibody. In another embodiment, the isotype of the antibody is IgG, optionally an IgG1. In one embodiment, the antibody is chimeric, e.g. contains a non-murine, optionally a human, constant region. In another embodiment, the antibody does not substantially bind to human TLR4, e.g., in paraffin-embedded tissue sections. In another embodiment, the antibody comprises a light chain comprising one, two or all three CDRs of the 40F9 light chain variable region sequence of SEQ ID NO:3. In another embodiment, the antibody comprises a heavy chain comprising one, two or all three CDRs of the 40F9 heavy chain variable region sequence of SEQ ID NO:4. In another embodiment, the antibody comprises a light chain having a CDR comprising an amino acid sequence of any one of SEQ ID NOS:5 to 7. In another embodiment, the antibody comprises a heavy chain having a CDR comprising an amino acid sequence of any one of SEQ ID NOS:8 to 10. In another embodiment, the antibody is 40F9 or a fragment or derivative thereof.

In another embodiment, the antibody is an antibody fragment selected from Fab, Fab', Fab'-SH, F(ab')$_2$, Fv, diabodies, single-chain antibody fragment, or a multispecific antibody comprising multiple different antibody fragments. In another embodiment, the antibody is conjugated or covalently bound to a detectable moiety. In another embodiment, the antibody specifically binds to a healthy human tissue selected from the group consisting of skin, cerebellum, breast, lung, esophagus, stomach, ileum, jejunum, duodenum, colon, liver, pancreas, testis, spleen, thymus, and tonsil.

In another aspect, the present invention provides kits comprising any of the anti-TLR3 antibodies of the invention, preferably together with instructions for their use, e.g., according to the therapeutic or diagnostic methods provided herein. In one embodiment, the kit further comprises a labeled secondary antibody that specifically recognizes the primary anti-TLR3 antibodies. In one such embodiment, the secondary antibody is conjugated to HRP or AP. In another embodiment, the HRP or AP is conjugated to a polymer.

In another aspect, the present invention provides a cell, e.g. a hybridoma, producing an anti-TLR3 antibody of the invention. In one embodiment, the cell is clone 40F9. In a related aspect, the present invention provides a hybridoma comprising: a) a B cell from a non-human mammalian host that has been immunized with an antigen that comprises the TLR3 epitope specifically recognized by the 40F9 antibody, fused to b) an immortalized cell, wherein the hybridoma produces a monoclonal antibody that specifically binds to the epitope.

In one embodiment of either of these aspects, the monoclonal antibody binds to the same epitope as antibody 40F9. In a particularly preferred embodiment, the hybridoma produces antibody 40F9.

In another aspect, the present invention provides a method of producing an antibody that specifically binds to TLR3 in paraffin-embedded tissues, said method comprising the steps of: a) immunizing a non-human mammal with an immunogen comprising a human TLR3 polypeptide; and b) preparing antibodies from said immunized animal that compete for binding to said TLR3 polypeptide with antibody 40F9.

In one embodiment, the antibodies prepared in step (b) are monoclonal antibodies. In another embodiment, the method further comprise a step in which the ability of said antibodies to specifically bind to human TLR3 polypeptides in paraffin-embedded tissue sections is assessed. In one embodiment, the ability of the antibodies to bind to other TLR family members is assessed, optionally in paraffin-embedded tissue sections. In one embodiment, the ability of the antibodies to bind to TLR4 is assessed. In another embodiment, the method further comprises the step of making fragments or derivatives of the selected monoclonal antibodies. In one embodiment, the fragments or derivatives are selected from the group consisting of Fab, Fab', Fab'-SH, F(ab')$_2$, Fv, diabodies, single-chain antibody fragment, multispecific antibodies comprising multiple different antibody fragments, humanized antibodies, and chimeric antibodies. In another embodiment, the non-human mammal is a mouse.

In another aspect, the present invention provides a method of detecting the level of TLR3 in a paraffin-embedded tissue sample, the method comprising the steps of a) contacting the tissue sample with an anti-TLR3 antibody of the invention; and b) detecting the presence of the bound antibody in the tissue sample.

In one embodiment, the antibody is a monoclonal antibody that competes for binding with antibody 40F9. In another embodiment, the antibody is antibody 40F9. In another embodiment, the tissue sample comprises a human tissue selected from the group consisting of skin, cerebellum, breast, lung, esophagus, stomach, ileum, jejunum, duodenum, colon, liver, pancreas, testis, spleen, thymus, and tonsil. In another embodiment, the tissue is a tumor tissue selected from the group consisting of breast, lung, esophagus, stomach, larynx, kidney, and cervix. In another embodiment, the tissue is breast tissue, and the patient has breast cancer. In another embodiment, the tissue comprises melanoma cells. In another embodiment, the biological sample is taken from a patient, and the method is performed for diagnostic purposes. In another embodiment, the biological sample is taken from a healthy individual.

In another embodiment, the antibody is conjugated or covalently bound to a detectable moiety. In another embodiment, the TLR3 levels are detected using a secondary antibody that specifically binds to said antibody. In another embodiment, the secondary antibody is covalently linked to HRP or AP. In another antibody, the HRP or AP is bound to a polymer.

In another aspect, the present invention provides a method of treating a patient with cancer, the method comprising a) providing a paraffin-embedded cancer tissue sample from the patient; b) detecting TLR3 levels in the tissue sample; and c) if TLR3 expression is detected in the sample, administering a TLR3 ligand to the patient.

In one embodiment, the TLR3 levels are detected using a monoclonal antibody that competes for binding with antibody 40F9. In another embodiment, the antibody is antibody 40F9. In another embodiment, in step c) a TLR3 ligand is administered to the patient if the level of TLR3 detected in step b) is elevated. In another embodiment, the cancerous tissue is selected from the group consisting of breast, lung, esophagus, stomach, larynx, kidney, and cervix. In another embodiment, the tissue is breast tissue, and the patient has breast cancer. In another embodiment, the tissue is a melanoma.

In another embodiment, the antibody is conjugated or covalently bound to a detectable moiety. In another embodiment, the TLR3 levels are detected using a secondary antibody that specifically binds to said antibody. In another embodiment, the secondary antibody is covalently linked to HRP or AP. In another embodiment, the TLR3 ligand is selected from the group consisting of double stranded RNA, poly I:C, and poly A:U.

In another embodiment, the method further comprises the step of administering to the patient an appropriate additional therapeutic agent selected from the group consisting of an immunomodulatory agent, a hormonal agent, a chemotherapeutic agent, an anti-angiogenic agent, an apoptotic agent, a targeting agent, and an adjunct compound.

These and additional advantageous aspects and features of the invention may be further described elsewhere herein.

BRIEF DESCRIPTION OF THE DRAWING

FIG. 1 shows results for commercial antibodies TLR3.7 from eBioscience, Inc. (graph 1) and goat pAb anti TLR3 from R&D Systems Inc. (graph 2), as tested in Biacore for binding to immobilized human TLR3 and TLR4 protein. Binding is represented ordinates (in resonance units (RU)), time is represented in axis (in seconds). While both antibodies showed binding to TLR3 over TLR4 protein in Biacore (binding on TLR3 chip represented in full line, binding on TLR4 chip represented in dotted line), these antibodies either showed no binding or were no longer specific for TLR3 when tested in tissue sections as detailed in the example section.

DETAILED DESCRIPTION OF THE INVENTION

Introduction

The present invention provides novel methods for producing and using antibodies and other compounds suitable for the diagnosis and treatment of disorders such as viral infection or cancer, particularly breast cancer, melanoma, cervical cancer, and hepatomas. Antibodies, antibody derivatives, antibody fragments, and hybridomas are encompassed, as are methods of producing the same and methods of treating and diagnosing patients using the antibodies and compounds.

The present invention is based, in part, on the discovery that monoclonal antibodies can be generated, such antibodies binding specifically and efficiently to TLR3-expressing cells in fixed, paraffin-embedded tissue samples. Generally, monoclonal antibodies directed against human TLR3 are either incapable of binding to TLR3 in paraffin-embedded tissue samples and/or are not specific for TLR3 and thus also bind to other polypeptides, including other TLR polypeptides such as TLR4. Overcoming this limitation, the inventors have identified epitopes present on human TLR3, including the epitope recognized by antibody 40F9, that are particularly accessible to binding in paraffin-embedded sections.

Accordingly, the present invention provides monoclonal antibodies, and derivatives and fragments thereof, that specifically bind to human TLR3 in paraffin-embedded tissue sections. In a preferred embodiment, the antibodies bind to the same epitope as, i.e. they compete for binding to, the epitope recognized by antibody 40F9. In addition to antibodies, antibody fragments, antibody derivatives, hybridomas and other cells, and methods of making each of these, the present invention also provides methods of detecting TLR3 levels in tissue and cell samples, as well as methods of treating and diagnosing conditions such as viral infections and cancer, particularly breast cancer, cervical cancer, hepatoma, or melanoma.

Typically, such diagnostic/therapeutic methods involve, first, detecting the prevalence of cells, such as cancer cells or immune cells, that express the TLR3 polypeptide, and then, if appropriate (e.g., if TLR3 expression is detected), administering one or more TLR3 ligands, e.g., dsRNA, poly I:U, or poly A:U. When the methods are used for the diagnosis or treatment of cancer, e.g., breast cancer, melanoma, cervical cancer, or hepatoma, then the tissue sample will typically comprise cancer cells obtained by, e.g., biopsy, and the TLR3 ligands will be administered to induce the apoptosis of the TLR3-expressing tumor cells. In the case of viral infection or other condition (bacterial or other infection, or other types of cancer), the methods can involve the detection of TLR3 on immune cells, and the TLR3 ligands administered to activate TLR3, leading to an immune reaction (involving innate or adaptive immunity) that can target the infected or cancer cells for destruction. It will be appreciated that these two methods are not exclusive, i.e. administering TLR3 ligands in the treatment of cancer can both activate the immune system via the TLR3 receptor and trigger apoptosis in TLR3-expressing tumor cells.

As the present antibodies are specific for TLR3, they can also be used for other purposes, including purifying TLR3 or TLR3-expressing cells, modulating (e.g. activating or inhibiting) TLR3 receptors in vitro, ex vivo, or in vivo, targeting TLR3-expressing cells for destruction in vivo, or specifically labeling/binding TLR3 in vivo, ex vivo, or in vitro, including for methods such as immunoblotting, FACS analysis, and immunoprecipitation.

DEFINITIONS

As used herein, "TLR3" ligands refer to any compound that can specifically bind to and alter the activity of TLR3 in vitro, ex vivo, or in vivo. The compound can be a naturally occurring ligand, e.g., dsRNA, or a synthetic ligand such as poly-IC or polyAU. The compound can be any type of molecule, including inorganic or organic compounds or elements, including proteins (such as antibodies), nucleic acids, carbohydrates, lipids, or any other molecular entity. Further, such compounds can modulate TLR3 receptors in any way, including activating or inhibiting, and by any mechanism, including by binding to the receptor and triggering or shutting off activity in a manner similar to a naturally occurring ligand, or by binding to the receptor and blocking access to other ligands. Preferably, the ligand activates the receptor, and as such can be used to induce the apoptosis of TLR3-expressing tumor cells.

As used herein, "paraffin-embedded tissue samples" (or "cells", "samples", "slides", or "tissues") can refer to cells or tissues taken from an organism or from in vitro that have been fixed, embedded in paraffin, sectioned, and transferred to a slide. It will be appreciated that fixation and paraffin embedding is a common practice that can vary in many aspects, e.g., with respect to the fixation and embedding methods used, with respect to the protocol followed, etc., and that for the purposes of the present invention any such variant method is encompassed, so long as it involves fixation of the tissue, embedding in paraffin or equivalent material, sectioning and transfer to a slide.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. TLR3, as assessed using either recombinant forms of the proteins, epitopes therein, or native proteins present on the surface of isolated target cells. Competitive binding assays and other methods for determining specific binding are further described below and are well known in the art.

When an antibody is said to "compete" or "bind to substantially the same epitope" as a particular monoclonal antibody (e.g. 40F9), it means that the antibody competes with the monoclonal antibody in a binding assay using either recombinant TLR3 molecules or surface expressed TLR3 molecules. For example, if a test antibody reduces the binding of 40F9 to a TLR3 polypeptide or TLR3-expressing cell in a binding assay, the antibody is said to "compete" with 40F9.

By "immunogenic fragment," it is herein meant any polypeptidic or peptidic fragment that is capable of eliciting an immune response such as (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable of eliciting an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

"Toxic" or "cytotoxic" peptides or small molecules encompass any compound that can slow down, halt, or reverse the proliferation of cells, decrease their activity in any detectable way, or directly or indirectly kill them. Preferably, toxic or cytotoxic compounds work by directly killing the cells, by provoking apoptosis or otherwise. As used herein, a toxic "peptide" can include any peptide, polypeptide, or derivative of such, including peptide- or polypeptide-derivatives with unnatural amino acids or modified linkages. A toxic "small molecule" can includes any toxic compound or element, preferably with a size of less than 10 kD, 5 kD, 1 kD, 750 D, 600 D, 500 D, 400 D, 300 D, or smaller.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes of the present invention, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The term "biological sample" as used herein includes but is not limited to a biological fluid (for example serum, lymph, blood), cell sample, or tissue sample (for example bone marrow or tissue biopsy including mucosal tissue such as from the gut, gut lamina propria, or lungs).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context of this invention, the term antibody that "binds" a common determinant designates an antibody that binds said determinant with specificity and/or affinity.

Producing Anti-TLR3 Antibodies

The antibodies of this invention specifically bind to TLR3 polypeptides, e.g., TLR3 polypeptides on the surface of human cells, particularly in paraffin-embedded tissue sections. The ability of the antibodies to specifically bind TLR3 polypeptides in paraffin-embedded tissue sections makes them useful for numerous applications, in particular for detecting TLR3 levels or distribution for diagnostic or therapeutic purposes, as described herein. In certain, preferred embodiments, the antibodies are used to determine the presence or level of TLR3 in tumor cells in a tissue sample taken from a patient, and, if TLR3 is detected on tumor cells in the tissue sample, TLR3 ligands such as dsRNA, poly-IC or poly-AU are administered to the patient, thereby inducing apoptosis of and/or cytokine/chemokine secretion of the TLR3-expressing tumor cells.

In a preferred embodiment, the invention provides an antibody that binds human TLR3, and competes for binding to human TLR3 with monoclonal antibody 40F9. Antibody 40F9 is produced by the cell deposited as 40F9.6 with the Collection Nationale de Culture de Microorganismes (CNCM), Institut Pasteur, 25 rue de Docteur Roux, F-75724 Paris on 6 Aug. 2008, under the number CNCM 1-4061.

"TLR3", "TLR3 polypeptide" and "TLR3 receptor", used interchangeably, are used herein to refer to Toll-Like Receptor 3, a member of the Toll-like receptor (TLRs) family. The amino acid sequence of human TLR3 is shown in SEQ ID NO:1 (NCBI accession number NP_003256, the disclosure of which is incorporated herein by reference). The human TLR3 mRNA sequence is described in NCBI accession number NM_003265. Human TLR3 sequences are also described in PCT patent publication no. WO 98/50547, the disclosure of which is incorporated herein by reference.

"TLR4", "TLR4 polypeptide" and "TLR4 receptor", used interchangeably, are used herein to refer to Toll-Like Receptor 4, a member of the Toll-like receptor (TLRs) family. The amino acid sequence of human precursor TLR4 including a signal peptide at amino acid residues 1-23 is shown in SEQ ID NO:2 (NCBI accession number NP_612564, the disclosure of which is incorporated herein by reference). Human TLR3 sequences are also described in THE UniProtKB/Swiss-Prot database and Swissprot accession number O00206, the disclosure of which is incorporated herein by reference.

The detection of the binding of the antibody to TLR3 can be performed in any of a number of ways. For example, the antibody can be directly labeled with a detectable moiety, e.g., a luminescent compound such as a fluorescent moiety, or with a radioactive compound, with gold, with biotin (which allows subsequent, amplified binding to avidin, e.g., avidin-AP), or with an enzyme such as alkaline phosphatase (AP) or horseradish peroxidase (HRP). Alternatively, and preferably, the binding of the antibody to the human TLR3 in the sample is assessed by using a secondary antibody that binds to the primary anti-TLR3 antibody and that itself is labeled, preferably with an enzyme such as horseradish peroxidase (HRP) or alkaline phosphatase (AP); however, it will be appreciated that the secondary antibodies can be labeled or detected using any suitable method. In a preferred embodiment, an amplification system is used to enhance the signal provided by the secondary antibody, for example the EnVision system in which the secondary antibodies are bound to a polymer (e.g., dextran) that is bound to many copies of a detectable compound or enzyme such as HRP or AP (see, e.g., Wiedorn et al. (2001) The Journal of Histochemistry & Cytochemistry, Volume 49(9): 1067-1071; Kämmerer et al., (2001) Journal of Histochemistry and Cytochemistry, Vol. 49, 623-630; the entire disclosures of which are herein incorporated by reference).

In an advantageous aspect, the invention provides an antibody that competes with monoclonal antibody 40F9 and recognizes, binds to, or has immunospecificity for substantially or essentially the same, or the same, epitope or "epitopic site" on a TLR3 molecule as monoclonal antibody 40F9. In other embodiments, the monoclonal antibody consists of, or is a derivative or fragment of, antibody 40F9.

It will be appreciated that, while preferred antibodies bind to the same epitope as antibody 40F9, the present antibodies can recognize and be raised against any part of the TLR3 polypeptide. For example, any fragment of TLR3, preferably but not exclusively human TLR3, or any combination of TLR3 fragments, can be used as immunogens to raise antibodies, and the antibodies of the invention can recognize epitopes at any location within the TLR3 polypeptide, so long as they can do so on paraffin-embedded sections as described herein. Preferably, the recognized epitopes are present on the cell surface, i.e. they are accessible to antibodies present outside of the cell. Most preferably, the epitope is the epitope specifically recognized by antibody 40F9. Further, antibodies recognizing distinct epitopes within TLR3 can be used in combination, e.g. to bind to TLR3 polypeptides with maximum efficacy and breadth among different individuals or in different tissue samples.

The antibodies of this invention may be produced by a variety of techniques known in the art. Typically, they are produced by immunization of a non-human animal, preferably a mouse, with an immunogen comprising a TLR3 polypeptide, preferably a human TLR3 polypeptide. The TLR3 polypeptide may comprise the full length sequence of a human TLR3 polypeptide, or a fragment or derivative thereof, typically an immunogenic fragment, i.e., a portion of the polypeptide comprising an epitope exposed on the surface of cells expressing a TLR3 polypeptide, preferably the epitope recognized by the 40F9 antibody. Such fragments typically contain at least about 7 consecutive amino acids of the mature polypeptide sequence, even more preferably at least about 10 consecutive amino acids thereof. Fragments typically are essentially derived from the extra-cellular domain of the receptor. In a preferred embodiment, the immunogen comprises a wild-type human TLR3 polypeptide in a lipid membrane, typically at the surface of a cell. In a specific embodiment, the immunogen comprises intact cells, particularly intact human cells, optionally treated or lysed. In another preferred embodiment, the polypeptide is a recombinant TLR3 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant.

Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with TLR3 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For preferred monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to TLR3 polypeptide gene products, preferably the epitope specifically recognized by antibody 40F9. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to TLR3 polypeptides, e.g., TLR3-expressing cells, in paraffin-embedded tissue sections, as described below.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to TLR3, particularly substantially or essentially the same epitope as monoclonal antibody 40F9, can be readily determined using any one of a variety of immunological screening assays in which antibody competition can be assessed. Many such assays are routinely practiced and are well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (40F9, for example) and test antibodies are admixed (or pre-adsorbed) and applied to a sample containing TLR3 polypeptides. Protocols based upon western blotting and the use of BIACORE analysis are suitable for use in such simple competition studies.

In certain embodiments, one pre-mixes the control antibodies (40F9, for example) with varying amounts of the test antibodies (e.g., about 1:10 or about 1:100) for a period of time prior to applying to the TLR3 antigen sample. In other embodiments, the control and varying amounts of test antibodies can simply be admixed during exposure to the TLR3 antigen sample. As long as one can distinguish bound from free antibodies (e.g., by using separation or washing techniques to eliminate unbound antibodies) and 40F9 from the test antibodies (e.g., by using species-specific or isotype-specific secondary antibodies or by specifically labeling 40F9 with a detectable label) one can determine if the test antibodies reduce the binding of 40F9 to the antigens, indicating that the test antibody recognizes substantially the same epitope as 40F9. The binding of the (labeled) control antibodies in the absence of a completely irrelevant antibody can serve as the control high value. The control low value can be obtained by incubating the labeled (40F9) antibodies with unlabelled antibodies of exactly the same type (40F9), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" with the labeled (40F9) antibody. Any test antibody that reduces the binding of 40F9 to TLR3 antigens by at least about 50%, such as at least about 60%, or more preferably at least about 70% (e.g., about 65-100%), at any ratio of 40F9:test antibody between about 1:10 and about 1:100 is considered to be an antibody that binds to substantially the same epitope or determinant as 40F9. Preferably, such test antibody will reduce the binding of 40F9 to the TLR3 antigen by at least about 90% (e.g., about 95%).

Competition can also be assessed by, for example, a flow cytometry test. In such a test, cells bearing a given TLR3 polypeptide can be incubated first with 40F9, for example, and then with the test antibody labeled with a fluorochrome or biotin. The antibody is said to compete with 40F9 if the binding obtained upon preincubation with a saturating amount of 40F9 is about 80%, preferably about 50%, about 40% or less (e.g., about 30%) of the binding (as measured by mean of fluorescence) obtained by the antibody without preincubation with 40F9. Alternatively, an antibody is said to compete with 40F9 if the binding obtained with a labeled 40F9 antibody (by a fluorochrome or biotin) on cells preincubated with a saturating amount of test antibody is about 80%, preferably about 50%, about 40%, or less (e.g., about 30%) of the binding obtained without preincubation with the antibody.

A simple competition assay in which a test antibody is pre-adsorbed and applied at saturating concentration to a surface onto which a TLR3 antigen is immobilized may also be employed. The surface in the simple competition assay is preferably a BIACORE chip (or other media suitable for surface plasmon resonance analysis). The control antibody (e.g., 40F9) is then brought into contact with the surface at a TLR3-saturating concentration and the TLR3 and surface binding of the control antibody is measured. This binding of the control antibody is compared with the binding of the control antibody to the TLR3-containing surface in the absence of test antibody. In a test assay, a significant reduction in binding of the TLR3-containing surface by the control antibody in the presence of a test antibody indicates that the test antibody recognizes substantially the same epitope as the control antibody such that the test antibody "cross-reacts" with the control antibody. Any test antibody that reduces the binding of control (such as 40F9) antibody to a TLR3 antigen by at least about 30% or more, preferably about 40%, can be considered to be an antibody that binds to substantially the same epitope or determinant as a control (e.g., 40F9). Preferably, such a test antibody will reduce the binding of the control antibody (e.g., 40F9) to the TLR3 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the TLR3 antigen is bound to the surface first, as it will be expected that the decrease in binding seen for the second antibody (assuming the antibodies are cross-reacting) will be of greater magnitude. Further examples of such assays are provided in, e.g., Saunal H. and al (1995) J. Immunol. Methods 183: 33-41, the disclosure of which is incorporated herein by reference.

Preferably, monoclonal antibodies that recognize a TLR3 epitope will react with an epitope that is present on a substantial percentage of or even all TLR3-expressing cells, e.g., dendritic cells, CD8+ T cells, cells of the skin, cerebellum, breast, lung, esophagus, stomach, ileum, jejunum, duodenum, colon, liver, pancreas, testis, spleen, thymus, or tonsil, but will not significantly react with other cells, i.e., immune or non-immune cells that do not express TLR3.

In preferred embodiments, the antibodies will bind to TLR3-expressing cells from an individual or individuals with a disorder associated with TLR3 expression e.g., tumors such as breast cancer, cervical cancer, hepatoma, melanoma, i.e., an individual that is a candidate for treatment with one of the herein-described methods (e.g., using a TLR3 ligand). Accordingly, once an antibody that specifically recognizes TLR3 on cells, preferably human cells, it can be tested for its ability to bind to TLR3-expressing cells taken from a patient with a condition such as breast cancer, melanoma, hepatoma, cervical cancer, or cancer of the lung, esophagus, stomach, or larynx.

In one embodiment of any of the methods of the present invention, tumor cells, e.g., melanoma cells, are first treated with a cytokine such as a type-1 interferon or with a TLR3 ligand prior to antibody binding, as such treatments can enhance TLR3 expression and thus facilitate antibody binding under some conditions.

In one embodiment, the antibodies of the invention are validated in an immunoassay to test their ability to bind to TLR3-expressing cells, e.g. tonsil cells. Preferably, the validation is performed by assessing the ability of the antibody to stain TLR3-expressing cells in a paraffin-embedded tissue section. For example, tonsil tissue samples are taken from a plurality of patients, and the ability of a given antibody to stain cells within the tissue is then assessed using standard methods well known to those in the art. Antibodies that are found to bind to a substantial proportion (e.g., 20%, 30%, 40%, 50%, 60%, 70%, 80% or more) of tissue samples known to contain TLR3-expressing cells, e.g. tonsil cells or certain tumors, from a significant percentage of individuals or patients (e.g., 30%, 40%, 50%, 60%, 70%, 80%, 90%, or more) are suitable for use in the present invention, both for diagnostic purposes to determine the presence or level of TLR3 cells in a patient or for use in the herein-described therapeutic methods, e.g., to detect TLR3-expressing tumor cells prior to the administration of TLR3 ligands. To assess the binding of the antibodies to the cells, the antibodies can either be directly or indirectly labeled. When indirectly labeled, a secondary, labeled antibody is typically added. Such methods are well known to those of skill in the art and are described further elsewhere herein.

While described in the context of 40F9 for the purposes of exemplification, it will be appreciated that the herein-described immunological screening assays and other assays can also be used to identify antibodies that compete with other anti-TLR3 antibodies, so long as they also bind to TLR3 in paraffin-embedded tissue samples.

Determination of whether an antibody binds within one of the epitope regions defined above can be carried out in ways known to the person skilled in the art. As one example of such mapping/characterization methods, an epitope region for an anti-TLR3 antibody may be determined by epitope "footprinting" using chemical modification of the exposed amines/carboxyls in the TLR3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance (NMR) epitope mapping, where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst Schering Res Found Workshop. 2004; (44): 149-67; Huang et al, Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downward, J Mass Spectrom. 2000 April; 35 (4): 493-503 and Kiselar and Downard, Anal Chem. 1999 May 1; 71 (9): 1792-801. Protease digestion techniques also can be useful in the context of epitope mapping and identification. Antigenic determinant-relevant regions/sequences can be determined by protease digestion, e.g. by using trypsin in a ratio of about 1:50 to TLR3 or o/n digestion at and pH 7-8, followed by mass spectrometry (MS) analysis for peptide identification. The peptides protected from trypsin cleavage by the anti-TLR3 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the TLR3 polypeptide that is not surface exposed and, accordingly, most likely not relevant in terms of immunogenicity/antigenicity. See, e.g., Manca, Ann Ist Super Sanita. 1991; 27: 15-9 for a discussion of similar techniques.

Once antibodies that are capable of binding to TLR3 in paraffin sections are identified, they will also typically be assessed, using standard methods including those described herein, for their ability to bind to other polypeptides, including unrelated polypeptides and other TLR family members (e.g., human TLR1, 2, or 4-10). Ideally, the antibodies only bind with substantial affinity to TLR3, e.g., human TLR3, and do not bind at a significant level to unrelated polypeptides or to other TLR family members (e.g., TLR2 or TLR4). However, it will be appreciated that, as long as the affinity for TLR3 is substantially greater (e.g., 5×, 10×, 50×, 100×, 500×, 1000×, 10,000×, or more) than it is for other TLR family members (or other, unrelated polypeptides), then the antibodies are suitable for use in the present methods. The preferred antibodies of the invention do not substantially bind to human TLR4, e.g. do not stain samples (e.g. paraffin-embedded samples) which express TLR4 and do not express TLR3. Human TLR4, a receptor for lipopolysaccharide (LPS) is described in OMIM Accession number 603030, and mRNA and amino acid sequences are provided in Genbank Accession number U88880 and AAC34135, as well as in Rock et al. (1998) P.N.A.S. USA 95(2): 588-593, the disclosures of which are incorporated herein by reference.

The binding of the antibodies to TLR3-expressing cells can also be assessed in non-human primates, e.g. cynomolgus monkeys, or other mammals such as mice. The invention therefore provides an antibody, as well as fragments and derivatives thereof, wherein said antibody, fragment or derivative specifically binds to TLR3 polypeptides at the surface of human cells present in a paraffin-embedded tissue section, and which furthermore binds to TLR3 expressing cells from non-human primates, e.g., cynomolgus monkeys. In certain embodiments, the non-human primate is a model for a TLR3-associated condition such as breast cancer or melanoma.

Upon immunization and production of antibodies in a vertebrate or cell, particular selection steps may be performed to isolate antibodies as claimed. In this regard, in a specific embodiment, the invention also relates to methods of producing such antibodies, comprising: (a) immunizing a non-human mammal with an immunogen comprising a TLR3 polypeptide; and (b) preparing antibodies from said immunized animal; and (c) selecting antibodies from step (b) that are capable of binding said TLR3 polypeptide in a paraffin-embedded tissue sample. In one embodiment, the method further comprises a step (d), selecting antibodies from (b) that are capable of competing for binding to TLR3 with antibody 40F9.

In preferred embodiments, the antibodies prepared according to the present methods are monoclonal antibodies. In preferred embodiments, the non-human animal used to produce antibodies according to the methods of the invention is a mammal, such as a rodent, bovine, porcine, horse, rabbit, goat, or sheep.

According to an alternate embodiment, the DNA encoding an antibody that binds an epitope present on TLR3 polypeptides is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the invention, e.g., antibody 40F9, can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody.

Recombinant expression in bacteria of DNA encoding the antibody is well known in the art (see, for example, Skerra et al., Curr. Opinion in Immunol., 5, pp. 256 (1993); and Pluckthun, Immunol. 130, pp. 151 (1992).

Antibody 40F9

In any of the embodiments herein, antibody 40F9 can be characterized by its amino acid sequence and/or nucleic acid sequence encoding it. The amino acid sequences of variable regions of the heavy and light chains for antibody 40F9 are listed in SEQ ID NOS:3 and 4, respectively. SEQ ID NO:3 shows the 40F9 light chain variable region (40F9VL) which was obtained as a potential rearrangement of VKappa bd2 (amino acid positions 1-102)/JK2 (amino acid positions 102-113)/Ckappa SEQ ID NO: 4 shows the 40F9 heavy chain variable region (40F9VK) which was obtained as a potential rearrangement of VH9-10 (amino acid positions 1-98)/DSP2.2 (amino acid positions 99-102)/JH2 (amino acid positions 103-113)/Cgamma1. In a specific embodiment, the antibody binds essentially the same epitope or determinant as one of monoclonal antibodies 40F9. In one preferred embodiment, the monoclonal antibody comprises the Fab or F(ab')$_2$ portion of 40F9. According to another preferred embodiment, the monoclonal antibody comprises the three CDRs of the variable heavy chain region of 40F9 (CDR1=amino acids 24 to 39 of SEQ ID NO:3; CDR2=amino acids 55 to 61 of SEQ ID NO:3; CDR3=amino acids 94-102 of SEQ ID NO:3). Also provided is a monoclonal antibody that comprises the variable heavy chain region of 40F9 (40F9VH; SEQ ID NO:3). According to another preferred embodiment, the monoclonal antibody comprises the three CDRs of the variable light chain region of 40F9 (CDR1=amino acids 27 to 35 of SEQ ID NO:4; CDR2=amino acids 52 to 66 of SEQ ID NO:4; CDR3=amino acids 99-103 of SEQ ID NO:4). Also provided is a monoclonal antibody that comprises the variable light chain region of 40F9 (40F9VK; SEQ ID NO:4).

In another preferred embodiment, the antibody comprises a light chain comprising one, two or three of the CDRs of the variable light chain region of 40F9. In one embodiment, the CDRs of the variable light chain region comprise an amino acid sequence selected from the group consisting of: KSSQS-LLDSDGKTYLN (SEQ ID NO:5; CDR1); LVSKLDS (SEQ ID NO:6; CDR2); and WQGIHLPYT (SEQ ID NO:7; CDR3), or any sequence of 3, 4, 5, 6, 7, 8, 9, 10, 11, 12, 13, 14, 15 or 16 contiguous amino acids thereof (to the extent such sequence is consistent with the length of the SEQ ID), or any sequence which is at least 50%, 60%, 70%, 80% or 90% identical thereto over the length of the aforementioned CDR sequence. In another preferred embodiment, the antibody comprises a light chain comprising one, two or three of the CDRs of the variable heavy chain region of 40F9. In one embodiment, the CDRs of the variable heavy chain region comprise an amino acid sequence selected from the group consisting of: YTFTNYGMN (SEQ ID NO:8; CDR1); NANTGEPTYAEEFKG (SEQ ID NO:9; CDR2); and DYDY (SEQ ID NO:10; CDR3), or any sequence of 3, 4, 5, 6, 7, 8, 9, 10, 11, 12, 13, 14 or 15 contiguous amino acids thereof (to the extent such sequence is consistent with the length of the SEQ ID), or any sequence which is at least 50%, 60%, 70%, 80% or 90% identical thereto over the length of the sequence of the aforementioned CDR sequence. CDR1 of the heavy chain in SEQ ID NO:8 is defined according to the Kabat definition; however heavy chain CDR1 can alternatively be defined according to the Chothia definition as KASGYTFTNYGMN (SEQ ID NO:11; CDR1). It will therefore be appreciated that in any of the embodiments herein, the heavy chain CDR1 described in SEQ ID NO:11 may be substituted for the CDR1 described in SEQ ID NO:8. Optionally any one or more of said light or heavy chain CDRs may contain one, two, three, four or five amino acid modifications (e.g. substitutions, insertions or deletions). In another preferred embodiment the antibody is 40F9.

Fragments and Derivatives of the Present Monoclonal Antibodies

Fragments and derivatives of antibodies of this invention (which are encompassed by the term "antibody" or "antibodies" as used in this application, unless otherwise stated or clearly contradicted by context), preferably a 40F9-like antibody, can be produced by techniques that are known in the art. "Fragments" comprise a portion of the intact antibody, generally the antigen binding site or variable region. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments.

Fragments of the present antibodies can be obtained using standard methods. For instance, Fab or F(ab')$_2$ fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, 16 (3): 106-119 (2001) and Delgado et al, Br. J. Cancer 73 (2): 175-182 (1996), the disclosures of which are incorporated herein by reference.

Alternatively, the DNA of a hybridoma producing an antibody of the invention, preferably a 40F9-like antibody, may be modified so as to encode a fragment of the invention. The modified DNA is then inserted into an expression vector and used to transform or transfect an appropriate cell, which then expresses the desired fragment.

In certain embodiments, the DNA of a hybridoma producing an antibody of this invention, preferably a 40F9-like antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention, preferably a 40F9-like antibody, is humanized. "Humanized" forms of antibodies according to this invention are specific chimeric immunoglobulins, immunoglobulin chains or fragments thereof (such as Fv, Fab, Fab', F(ab')$_2$, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et Nature, 332, pp. 323 (1988); Presta, Curr. Op. Struct. Biol., 2, pp. 593 (1992); Verhoeyen et Science, 239, pp. 1534; and U.S. Pat. No. 4,816, 567, the entire disclosures of which are herein incorporated by reference.) Methods for humanizing the antibodies of this invention are well known in the art.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et J. Immunol., 51, pp. 1993)).

It is further important that antibodies be humanized with retention of high affinity for TLR3 receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et Nature 362 (1993) 255), or by selection of antibody repertoires using phage display methods. Such techniques are known to the skilled person and can be implemented starting from monoclonal antibodies as disclosed in the present application.

The antibodies of the present invention, preferably a 40F9-like antibody, may also be derivatized to "chimeric" antibodies (immunoglobulins) in which a portion of the heavy/light chain(s) is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A., pp. 6851 (1984)).

While the present antibodies all have the ability to bind to TLR3 in paraffin embedded or equivalent tissue samples, they can also be used for other purposes such as to label TLR3 in vitro, ex vivo, or in vivo, to purify TLR3-expressing cells, or to target TLR3-expressing cells for killing, e.g., in vivo. Accordingly, other derivatives of the present antibodies that fall within the scope of this invention include functionalized antibodies, i.e., antibodies that are conjugated or covalently bound to a toxin, such as ricin, diphtheria toxin, abrin, or *Pseudomonas* exotoxin; to a detectable moiety, such as a fluorescent moiety, a radioisotope, or an imaging agent; or to a solid support, such as agarose beads or the like. Methods for conjugation or covalent bonding of these other agents to antibodies are well known in the art. Conjugation to a toxin is useful for targeted killing cells displaying TLR3 receptors on its cell surface, e.g. certain tumor cells such as melanomas or those of the breast, lung, esophagus, stomach, larynx, kidney, or cervix. In such embodiments, typically a biopsy will be performed initially to assess whether the tumor cells express TLR3, e.g., using the detection methods described herein. If TLR3 is indeed detected on the surface of the tumor cells, then, together with or as an alternative to the administration of TLR3 ligands as described elsewhere herein, cytotoxic antibodies can be administered. Once the cytotoxic antibody of the invention binds to the cell surface of TLR3-expressing cells, e.g., TLR3-expressing tumor cells, it is internalized and the toxin is released inside of the cell, selectively killing that cell.

Conjugation to a detectable moiety is useful, inter alia, when an antibody of the invention is used for diagnostic purposes. Such purposes include, but are not limited to, assaying biological samples, e.g., a blood sample or tissue biopsy, for the presence of TLR3-expressing cells, and detecting the presence, level, or activity of TLR3-expressing cells in an individual. Such assay and detection methods can be used in the diagnostic/therapeutic methods of the invention, e.g., involving detecting TLR3 expression in tumor cells of a patient and subsequently administering a TLR3 ligand, e.g., dsRNA, polyIC, polyAU, to the patient to induce apoptosis of the TLR3-expressing cells.

In certain embodiments, the present antibodies are used to purify TLR3-expressing cells from a biological sample. Biological samples can be obtained from a patient, e.g. for diagnostic or ex vivo therapeutic purposes, or from individuals or non-human primates to obtain a source of such cells for research purposes.

In one such embodiment, labeled antibodies of the invention can be used in FACS sorting to purify or isolate TLR3-expressing cells from a biological sample. Alternatively, in some embodiments conjugation of an antibody of this invention to a solid support can be useful as a tool for affinity purification of cells bearing a TLR3 receptor on their cell surface from a biological sample, such as a blood sample or cells from a tissue biopsy from an individual. This method of purification is another alternate embodiment of the present invention, as is the resulting purified population of cells.

Regardless of the method used to isolate or purify the TLR3-expressing cells, the ability to do so is useful for numerous purposes, e.g. to diagnose a TLR3-associated disorder by assessing the number or activity of TLR3-expressing cells, e.g., prior to administration of TLR3 ligands as described herein. Also, purifying or isolating cells can be performed to evaluate the sensitivity of the TLR3-expressing cells undergoing apoptosis in the presence of TLR3 ligands. Further, purified TLR3-expressing cells are useful in a research context, e.g., to better characterize the cells and their various properties and behaviors, as well as to identify compounds or methods that can be used to modulate their behavior, activity, survival, or proliferation.

Preparation and Staining of Paraffin-Embedded Tissue Sections

The present antibodies have the particular property of being able to efficiently and specifically bind to TLR3 polypeptides present in fixed tissue or cell samples. Without being bound by the following theory, it is believed that fixation, e.g., formalin fixation, may destroy many epitopes present on the polypeptide, eliminating the ability of many antibodies to specifically bind to the polypeptide; alternatively, the fixation/embedding procedure may expose or render particularly accessible particular epitopes that are not necessarily readily present for antibody binding by other methods, e.g., western blot, FACS, etc. The present antibodies are not only able to bind such epitopes with high affinity, but preferably also do so with high specificity, e.g., they do not substantially bind to other polypeptides, e.g., unrelated proteins or other TLR family members such as TLR4.

Various methods of preparing and using such tissue preparations are well known in the art, and any suitable method or type of preparation can be used. It will be appreciated, for example, that the present antibodies can be used with any fixed cell or tissue preparation, and that they are not limited by the particular fixation or embedding method used. For example, while the most common fixation procedure involves formalin (e.g., 10%), alternative methods such as paraformaldehyde (PFA), Bouin solution (formalin/picric acid), alcohol, zinc-based solutions (for one example, see, e.g., Lykidis et al., (2007) Nucleic Acids Research, 2007, 1-10, the entire disclosure of which is herein incorporated in its entirety), and others (see, e.g., the HOPE method, Pathology Research and Practice, Volume 197, Number 12, December 2001, pp. 823-826(4), the entire disclosure of which is herein incorporated by reference). Similarly, while paraffin is preferred, other materials can be used for embedding as well, e.g., polyester wax, polyethylene glycol based formulas, glycol methacrylates, JB-4 plastics, and others. For review of methods for preparing and using tissue preparations, see, e.g., Gillespie et al., (2002) Am J. Pathol. 2002 February; 160(2): 449-457; Fischer et al. CSH Protocols; 2008; Renshaw (2007), Immunohistochemistry: Methods Express Series; Bancroft (2007) Theory and Practice of Histological Techniques; and PCT patent publication no. WO06074392; the entire disclosures of which are herein incorporated by reference).

Generally, the tissue (or cells) to be examined is obtained by, e.g., biopsy from a tumor tissue (e.g., breast tumor, melanoma) or from a healthy tissue, and sections (e.g., 3 mm thick or less) and fixed using formalin or an equivalent fixation method (see supra). The time of fixation depends on the application and is not critical for the purposes of the present invention, but can range from several hours to 24 or more hours. Following fixation, the tissue is embedded in paraffin (or equivalent material), and very thin sections (e.g., 5 microns) are cut in a microtome and then mounted onto, preferably coated, slides. The slides are then dried, e.g., air dried.

Fixed and embedded tissue sections on slides can be dried and stored indefinitely. For immunohistochemistry, the slides are deparaffinized and then rehydrated. For example, they are subjected to a series of washes with, initially, xylene, and then xylene with ethanol, and then with decreasing percentages of ethanol in water.

Before antibody staining, the tissues can be subjected to an antigen retrieval step, e.g., enzymatic or heat-based, in order to break methane bridges that form during fixation and which can mask epitopes. In a preferred embodiment, a treatment in boiling 10 mM citrate buffer, pH 6, is used.

Once the slides have been rehydrated and antigen retrieval has been ideally performed, they can be incubated with the primary antibody. First, the slides are washed with, e.g., TBS, and then, following a blocking step with, e.g., serum/BSA, the antibody can be applied. The concentration of the antibody will depend on its form (e.g., purified), its affinity, the tissue sample used, but a suitable concentration is, e.g., 1-10 μg/ml. In one embodiment, the concentration used is 10 μg/ml. The time of incubation can vary as well, but an overnight incubation is typically suitable. Following a post-antibody washing step in, e.g., TBS, the slides are then processed for detection of antibody binding.

The detection method used will depend on the antibody, tissue, etc. used, and can involve detection of a luminescent or otherwise visible or detectable moiety conjugated to the primary antibody, or through the use of detectable secondary antibodies. Methods of antibody detection are well known in the art and are taught, e.g., in Harlow et al., Antibodies: A Laboratory Manual, Cold Spring Harbor Laboratory Press, 1st edition (Dec. 1, 1988); Fischer et al. CSH Protocols; 2008; Renshaw (2007), Immunohistochemistry: Methods Express Series; Bancroft (2007) Theory and Practice of Histological Techniques; PCT patent publication no. WO06074392; the entire disclosure of each of which is herein incorporated in its entirety.

In a preferred embodiment, the binding of the primary antibody is detected by binding a labeled secondary antibody, preferably a secondary antibody covalently linked to an enzyme such as HRP or AP. In a particularly preferred embodiment, the signal generated by binding of the secondary antibody is amplified using any of a number of methods for amplification of antibody detection. For example, the EnVision method can be used, (see, e.g., U.S. Pat. No. 5,543,332 and European Patent no. 594,772; Kämmerer et al., (2001) Journal of Histochemistry and Cytochemistry, Vol. 49, 623-630; Wiedorn et al. (2001) The Journal of Histochemistry & Cytochemistry, Volume 49(9): 1067-1071; the entire disclosures of which are herein incorporated by reference), in which the secondary antibodies are linked to a polymer (e.g., dextran) that is itself linked to many copies of AP or HRP.

Assessing the Ability of Antibodies to Modulate TLR3-Expressing Cell Activity

In certain embodiments, the antibodies of this invention are able to modulate, e.g., activate or inhibit, the activity or behavior of TLR3-expressing cells, such as immune cells or tumor cells. For example, TLR3 activation can trigger various signaling cascades and alter the activity or expression of numerous regulatory molecules in cells, e.g., TRIF, MyD88, NFκB, ultimately leading to the secretion of interferon and other cytokines, and associated activities such as NK cell activation, the enhancement of CD8+ T cells, and antigen cross-priming by dendritic cells. Antibodies capable of stimulating TLR3 and triggering an immune response in any of these ways are referred to herein as "activating" or "stimulatory" antibodies. They are useful, e.g., for treating or preventing a condition caused by a decrease in TLR3-expressing cell activity or number, or where increased TLR3-expressing cell activity can ameliorate, prevent, eliminate, or in any way improve the condition or any symptom thereof. Other antibodies, on the other hand, can inhibit the activation of TLR3-expressing cells, e.g., they can block the binding of endogenous ligands such as dsRNA to TLR3, or block the ability of TLR3 protein to form homodimers in the presence of dsRNA, thus initiating a signaling cascade. These antibodies are thus referred to as "neutralizing" or "inhibitory" or "blocking" antibodies. Such antibodies are useful, inter alia, for decreasing TLR3-expressing immune cell activity, e.g., for the treatment or prevention of conditions involving excess TLR3-expressing cell activity or number, or where decreased TLR3-expressing cell activity can ameliorate, prevent, eliminate, or in any way improve the condition or any symptom thereof.

In a preferred embodiment, the antibodies are capable of stimulating TLR3 receptors on tumor cells, e.g., breast cancer cells, melanoma cells, hepatoma cells, or cervical cancer cells, causing their death via apoptosis. As such, the antibodies can be used in the treatment of the cancer, e.g., breast cancer, cervical cancer, hepatoma, or melanoma, e.g., by administering the antibodies systemically or topically to the site of the cancer. Typically, in such embodiments, the expression of TLR3 in the cancer cells will be assessed in a prior step according to the present methods, e.g., using the present antibodies to detect TLR3 expression, e.g., in a biopsy or other sample of the cancerous tissue or cells.

Any of a large number of assays, including molecular, cell-based, and animal-based models, can be used to assess the ability of anti-TLR3 antibodies to modulate TLR3-expressing cell activity. For example, cell-based assays can be used in which cells expressing TLR3 are exposed to dsRNA, polyIC, or poly AU, or another ligand (or cells expressing the ligand), and the ability of the antibody to disrupt the binding of the ligand or the stimulation of the receptor (as determined, e.g., by examining any of the TLR3 cell activities addressed herein, such as interferon expression, NFκB activity, NK cell activation, etc.) is assessed.

The activity of TLR3-expressing cells can also be assessed in the absence of a ligand, by exposing the cells to the antibody itself and assessing its effect on any aspect of the cells' activity or behavior. In such assays, a baseline level of activity (e.g., cytokine production, proliferation, see below) of the TLR3-expressing cells is obtained in the absence of a ligand, and the ability of the antibody or compound to alter the baseline activity level is detected. In one such embodiment, a high-throughput screening approach is used to identify compounds capable of affecting the activation of the receptor.

Any suitable physiological change that reflects TLR3 activity can be used to evaluate test antibodies or antibody derivatives. For example, one can measure a variety of effects, such as changes in gene expression (e.g., NFκB-responding genes), protein secretion (e.g., interferon), cell growth, cell proliferation, pH, intracellular second messengers, e.g., $Ca^{2+}$, IP3, cGMP, or cAMP, or activity such as ability to activate NK cells. In one embodiment, the activity of the receptor is assessed by detecting production of TLR3-responsive cytokines.

In another embodiment, the effect of the present antibodies on TLR3-expressing cells is assessed in non-human primates in vivo. For example, a pharmaceutical composition comprising an anti-TLR3 antibody of the present invention is administered to a non-human primate that is either healthy or affected by a TLR3-associated condition, e.g. a viral infection (in which activation of TLR3 could trigger an immune response and help fight the infection) or cancer (in which activation of TLR3 on tumor cells could lead to apoptosis of the cells), and the effect of the administration on, e.g., the number or activity of TLR3-expressing cells in the primate, or on the progression of the condition is assessed. Any antibody or antibody derivative or fragment that effects a detectable change in any of these TLR3-related parameters is a candidate for use in the herein-described methods.

In any of the herein-described assays, an increase or decrease of 5%, 10%, 20%, preferably 30%, 40%, 50%, most preferably 60%, 70%, 80%, 90%, 95%, or greater in any detectable measure of TLR3-stimulated activity in the cells indicates that the test antibody is suitable for use in the present methods.

Compositions and Uses in Diagnostics, Prognostics and Therapy

As demonstrated herein, the antibodies of the invention are particularly effective at detecting cells which express TLR3 polypeptides (e.g. melanomas, breast cancers, etc.), and without non-specific staining on tissues that do not express TLR3 polypeptides. The antibodies will therefore have advantages for use in the diagnosis, prognosis and/or prediction of pathologies involving TLR3-expressing cells. For example, cancer in patients can be characterized or assessed using an antibody of the invention. This can be useful to determine whether a patient has a pathology characterized by cells which express TLR3 polypeptides. The method can also be useful to determine whether a patient having such pathology can be treated with a therapy effective in cells which express TLR3. For example the method can be used to determine if a patient will respond to an antigen binding compound that binds TLR3 (e.g. any antibody) or that modulates (e.g. activates or inhibits) TLR3 or a TLR3-linked signaling pathway.

The antibodies described herein can therefore be used for the detection, preferably in vitro, of the presence of TLR3- expressing cells, optionally of a pathology where TLR3-expressing cells are present (e.g. cancer, infection, inflammatory or autoimmune disorders). Such a method will typically involve contacting a biological sample (e.g. paraffin-embedded tissue section) from a patient with an antibody according to the invention and detecting the formation of immunological complexes resulting from the immunological reaction between the antibody and the biological sample. The complex can be detected directly by labelling the antibody according to the invention or indirectly by adding a molecule which reveals the presence of the antibody according to the invention (secondary antibody, streptavidin/biotin tag, etc.). For example, labelling can be accomplished by coupling the antibody with radioactive or fluorescent tags. These methods are well known to those skilled in the art. Accordingly, the invention also relates to the use of an antibody according to the invention for preparing a diagnostic composition that can be used for detecting the presence of TLR3-expressing cells, optionally for detecting the presence of a pathology where TLR3-expressing cells are present, optionally for characterizing a cancer or other pathology, in vivo or in vitro.

In some embodiments, the antibodies of the invention will also be useful for predicting a cancer prognosis; a cancer prognosis, a prognostic for cancer or cancer progression comprises providing the forecast or prediction of (prognostic for) any one or more of the following: duration of survival of a subject susceptible to or diagnosed with a cancer, duration of recurrence-free survival, duration of progression free survival of a subject susceptible to or diagnosed with a cancer, response rate to treatment in a subject or group of subjects susceptible to or diagnosed with a cancer, and/or duration of response, degree of response, or survival following treatment in a subject.

The antibodies of the invention will also be generally useful for determining whether a subject is suitable for, or for predicting the response of a subject to, treatment with a therapeutic agent directed to a TLR3-expressing cell. Preferably the therapeutic agent is an antigen-binding fragment (e.g. an antibody, an antibody of the invention) that binds to or modulates (e.g. activates or inhibits) a TLR3 polypeptide.

The antibodies of the invention will also be useful, for example, for assessing the response of a subject having cancer to a treatment with a TLR3 ligand, e.g., a TLR3 agonist such as a dsRNA, polyIC, polyAU, or an activating anti-TLR3 antibody; such a method will typically involve assessing whether the patient has cancer cells that express a TLR3 polypeptide bound by an antibody of the invention, the expression of TLR3 polypeptide being indicative of a responder subject. A positive determination that a patient has cancer cells that express TLR3 polypeptides indicates that the patient will be a positive responder to treatment with the TLR3 ligand.

Also encompassed is a diagnostic or prognostic kit, in particular for cancer, comprising an antibody according to the invention. Optionally the kit comprises an antibody of the invention for use as a diagnostic or prognostic, and a TLR3 ligand (e.g. a TLR3 modulating agent, a TLR3 agonist or a TLR3 antagonist), optionally wherein the TLR3 ligand is an antibody or nucleic acid (e.g. dsRNA), for use as a therapeutic. Said kit can additionally comprise means by which to detect the immunological complex resulting from the immunological reaction between the biological sample and an antibody of the invention, in particular reagents enabling the detection of said antibody.

In preferred embodiments, the present antibodies are used in diagnostic, or combined diagnostic-therapeutic, methods, involving the detection of TLR3 in cells present on paraffin-embedded tissue samples. In particularly preferred embodiments, the tissue samples comprise tumor tissue, e.g., from breast, melanoma, lung, esophagus, stomach, larynx, kidney, or cervix. Typically, in such embodiments, a paraffin-embedded slide comprising tissue obtained from a biopsy from the patient will be provided, and the presence of TLR3 in the tissue will be assessed using the herein-described antibodies and methods. A detection of TLR3 in the tissue sample indicates that the patient is suitable for treatment with a TLR3 ligand, e.g., a TLR3 agonist such as a dsRNA, polyIC, polyAU, or an activating anti-TLR3 antibody. Preferably the TLR3 ligand is an agent capable of inducing apoptosis of TLR3-expressing cells (e.g. polyAU, polyIC). In other embodiments, the method may further comprise the additional step of administering to said patient the TLR3 ligand. In other embodiments, the method may further comprise the additional step of administering to said patient, in combination or addition to the TLR3 ligand, an appropriate additional therapeutic agent selected from an immunomodulatory agent, a hormonal agent, a chemotherapeutic agent, an anti-angiogenic agent, an apoptotic agent, a second antibody that binds to and modulates a TLR3 receptor, an anti-infective agent, a targeting agent, an anti-inflammation drug, a steroid, an immune system suppressor, an antibiotic, or an adjunct compound.

Certain compositions can also be used to induce the expression of TLR3 in cells, including TLR3 agonists (e.g. dsRNA such as polyAU) and IFN-alpha. The present antibodies are also useful in a method of sensitizing a cell or a patient to a treatment, e.g. with a TLR3 agonist, and/or to detect if a patient (or cell) is sensitized to treatment. Such methods can be useful in the treatment of cancers in particular. Typically, in such embodiments, the method comprises contacting a biological sample (e.g. a tumor sample) with, or administering to the patient, an effective amount of a composition capable of inducing TLR3 expression in a cell, providing a paraffin-embedded slide comprising tissue obtained from a biopsy from the patient, and assessing the presence of TLR3 in the tissue using the herein-described antibodies and methods. A detection of TLR3 in the tissue sample indicates that the patient has been sensitized to a treatment, e.g. with a TLR3 ligand. In other embodiments, the method may further comprise the additional step of administering to said patient the TLR3 ligand.

The present invention also provides pharmaceutical compositions that comprise an antibody, or a fragment and derivative thereof, wherein said antibody, fragment or derivative specifically binds to TLR3 polypeptides on the surface of cells, and optionally modulates the activity of TLR3-expressing cells comprising the polypeptides and, consequently, the activity or behavior of the cells expressing the polypeptides, e.g., TLR3-expressing tumor or immune cells. In certain embodiments, the antibodies stimulate the TLR3 and thus enhance the activity or proliferation of the cells, or induce their apoptosis. In other embodiments, the antibodies inhibit the TLR3, e.g., by blocking the interaction of an antigen or ligand such as dsRNA to the receptor, and thus inhibits the proliferation or activation of the cells. The composition further comprises a pharmaceutically acceptable carrier. Such compositions are also referred to as "antibody compositions" of the invention. In one embodiment, antibody compositions of this invention comprise an antibody disclosed in the antibody embodiments above. The antibody 40F9 is included within the scope of antibodies that may be present in the antibody compositions of this invention.

The invention further provides a method of modulating TLR3-expressing cell activity in a patient in need thereof, comprising the step of administering to said patient a composition according to the invention. In one embodiment, the cell activity is enhanced, wherein the patient has a disease or disorder wherein such enhancement may promote, enhance, and/or induce a therapeutic effect (or promotes, enhances, and/or induces such an effect in at least a substantial proportion of patients with the disease or disorder and substantially similar characteristics as the patient, as may determined by, e.g., clinical trials). Included in such embodiments are methods in which the antibodies are administered to induce the apoptosis of TLR3-expressing tumor cells. In another embodiment, the TLR3-expressing cell activity is inhibited, wherein the patient has a disease or disorder wherein such inhibition may promote, enhance, and/or induce a therapeutic effect (or promotes, enhances, and/or induces such an effect in at least a substantial proportion of patients with the disease or disorder and substantially similar characteristics as the patient—as may determined by, e.g., clinical trials).

In other embodiments, the method may comprise the additional step of administering to said patient an appropriate additional therapeutic agent selected from an immunomodulatory agent, a hormonal agent, a chemotherapeutic agent, an anti-angiogenic agent, an apoptotic agent, a second antibody that binds to and modulates a TLR3 receptor, an anti-infective agent, a targeting agent, an anti-inflammation drug, a steroid, an immune system suppressor, an antibiotic, or an adjunct compound. Such additional agents can be administered to said patient as a single dosage form together with said antibody, or as a separate dosage form. The dosage of the antibody (or antibody and the dosage of the additional therapeutic agent collectively) are sufficient to detectably induce, promote, and/or enhance a therapeutic response in the patient. Where administered separately, the antibody, fragment, or derivative and the additional therapeutic agent are desirably administered under conditions (e.g., with respect to timing, number of doses, etc.) that result in a detectable combined therapeutic benefit to the patient.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The antibodies of this invention may also be employed in a method of modulating, e.g. enhancing or inhibiting, the activity of TLR3-expressing cells in a patient or a biological sample. This method comprises the step of contacting said composition with said patient or biological sample. Such method will be useful for both diagnostic and therapeutic purposes.

For use in conjunction with a biological sample, the antibody composition can be administered by simply mixing with or applying directly to the sample, depending upon the nature of the sample (fluid or solid). The biological sample may be contacted directly with the antibody in any suitable device (plate, pouch, flask, etc.). For use in conjunction with a patient, the composition must be formulated for administration to the patient.

The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation. Patches may also be used.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Several monoclonal antibodies have been shown to be efficient in clinical situations, such as Rituxan Herceptin (Trastuzumab) or Xolair (Omalizumab), and similar administration regimens (i.e., formulations and/or doses and/or administration protocols) may be used with the antibodies of this invention. Schedules and dosages for administration of the antibody in the pharmaceutical compositions of the present invention can be determined in accordance with known methods for these products, for example, using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/mL and 500 mg/mL. However, it will be appreciated that these schedules are exemplary and that an optimal schedule and regimen can be adapted taking into account the affinity and tolerability of the particular antibody in the pharmaceutical composition that must be determined in clinical trials. Quantities and schedule of injection of an antibody in a pharmaceutical composition of this invention that saturate TLR3-expressing cells for 24 hours, 48 hours, 72 hours, or a week or a month will be determined considering the affinity of the antibody and its pharmacokinetic parameters.

According to another embodiment, the antibody compositions of this invention may further comprise another therapeutic agent, including agents normally utilized for the particular therapeutic purpose for which the antibody is being administered. The additional therapeutic agent will normally be present in the composition in amounts typically used for that agent in a monotherapy for the particular disease or condition being treated. Such therapeutic agents include, but are not limited to, therapeutic agents used in the treatment of cancers, therapeutic agents used to treat infectious disease, therapeutic agents used in other immunotherapies, cytokines (such as IL-2 or IL-15), anti-inflammation agents, steroids, immune system suppressors, antibiotics, and other antibodies and fragments thereof.

In another embodiment, two or more antibodies of this invention having different cross-reactivities, e.g. antibodies that specifically bind to distinct epitopes within the TLR3 polypeptide on paraffin-embedded tissue samples, are combined in a single composition so as to target as many distinct TLR3 gene products as possible, e.g. to account for diversity in the polypeptides within an individual or in different patients, and to do so as efficaciously as possible. In addition, an antibody composition of this invention may comprise multiple antibodies that recognize a single TLR3 epitope. Such combinations would again provide wider utility in a therapeutic setting or ensure optimal TLR3 staining in paraffin embedded tissue sections.

The invention also provides a method of modulating TLR3-expressing cell activity in a patient in need thereof, comprising the step of administering a composition according to this invention to said patient. The method is more specifically directed at increasing TLR3 cell activity in patients having a disease in which increased TLR3 cell activity is beneficial (e.g., infection such as a viral infection, or cancer in which the cancer cells express TLR3), or which is caused or characterized by insufficient TLR3 cell activity, or, contrarily, at decreasing TLR3 cell activity in patients having a disease in which decreased TLR3 cell activity is beneficial, or which is caused or characterized by excessive TLR3 cell activity.

Diseases and conditions in which the present methods can be used include cancer, other proliferative disorders, infectious disease, or immune disorders such as inflammatory diseases and autoimmune diseases. More specifically, the methods of the present invention are utilized for the treatment of a variety of cancers and other proliferative diseases including, but not limited to, carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute leukemia, B-cell lymphoma, T-cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias and promyelocytic leukemia; tumors origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors origin, including fibrosarcoma, rhabdomyoscaroma, and osteosarcoma; and other tumors, including melanoma, keratoacanthoma, seminoma, thyroid follicular cancer and teratocarcinoma. In preferred embodiments, the methods are used to diagnose or treat tumors selected from the group consisting of breast, melanoma, lung, esophagus, stomach, larynx, kidney, and cervix. In preferred embodiments, the cancer comprises TLR3-expressing cells, and the present antibodies and methods are used to detect TLR3 expression in the cells.

Other proliferative disorders in which the present methods can be used include for example hyperplasias, fibrosis (especially pulmonary, but also other types such as renal fibrosis), angiogenesis, psoriasis, atherosclerosis and smooth muscle proliferation in the blood vessels, such as stenosis or restenosis following angioplasty.

The antibodies of this invention can be used to treat or prevent infectious diseases, e.g., by detecting TLR3 levels in immune cells in vitro or ex vivo, and subsequently inducing TLR3 activity (in the case of a detection of TLR3) to activate the immune system. Targeted infections are preferably any infections caused by viruses, bacteria, protozoa, molds or fungi. Such viral infectious organisms include, but are not limited to, hepatitis type A, hepatitis type B, hepatitis type C, influenza, varicella, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus, echinovirus, arbovirus, huntavirus, coxsackie virus, mumps virus, measles virus, rubella virus, polio virus, and human immunodeficiency virus type I HIV-2).

Bacterial infections that can be treated according to this invention include, but are not limited to, infections caused by the following: *Staphylococcus; Streptococcus*, including *S. pyogenes*; Enterococci; *Bacillus*, including *Bacillus anthracis; Lactobacillus; Listeria; Corynebacterium diphtheriae; Gardnerella*, including *G. vaginalis; Nocardia; Streptomyces; vulgaris; Pseudomonas*, including *aeruginosa; Legionella; Neisseria*, including *N. meningitides; Flavobacterium*, including *F. meningosepticum; Brucella; Bordetella*, including *B. pertussis* and *B. bronchiseptica; Escherichia*, including *E. coli; Enterobacter; Serratia*, including *S. marcescens* and *S. liquefaciens; Edwardsiella; Proteus*, including *P. mirabilis* and *P. vulgaris; Streptobacillus*; Rickettsiaceae, including *R. rickettsii; Chlamydia*, including *C. psittaci; Mycobacterium*, including *M. tuberculosis, M. intracellulare, M. folluiturn, M. laprae, M. avium, M. bovis*, and *M. kansasii*; and *Nocardia*.

Protozoa infections that may be treated according to this invention include, but are not limited to, infections caused by leishmania, kokzidioa, and trypanosoma. A complete list of infectious diseases can be found on the website of the National Center for Infectious Disease (NCID) at the Center for Disease Control (CDC), which list is incorporated herein by reference.

Immune disorders treatable using the present methods include, inter alia, autoimmune disorders and inflammatory disorders, including, but not limited to, Crohn's disease, Celiac disease, ulcerative colitis, irritable bowel syndrome, acute disseminated encephalomyelitis (ADEM), Addison's disease, antiphospholipid antibody syndrome (APS), aplastic anemia, autoimmune hepatitis, Diabetes mellitus, Goodpasture's syndrome, Graves' disease, Guillain-Barré syndrome (GBS), Hashimoto's disease, lupus erythematosus, Multiple sclerosis, Myasthenia gravis, opsoclonus myoclonus syndrome (OMS), optic neuritis, Ord's thyroiditis, pemphigus, primary biliary cirrhosis, psoriasis, rheumatoid arthritis, Reiter's syndrome, Takayasu's arteritis, temporal arteritis, warm autoimmune hemolytic anemia, Wegener's granulomatosis, appendicitis, arteritis, arthritis, blepharitis, bronchiolitis, bronchitis, bursitis, cervicitis, cholangitis, cholecystitis, chorioamnionitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, gingivitis, hepatitis, hidradenitis suppurativa, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, and vulvitis.

The present antibodies can be included in kits, which may contain any number of antibodies and/or other compounds, e.g., 1, 2, 3, 4, 5, 6, 7, 8, 9, 10, or any other number of therapeutic antibodies and/or compounds, as well as, in certain embodiments, antibodies or other diagnostic reagents for detecting the presence of TLR3 in paraffin-embedded tissue samples. Such diagnostic antibodies will often be labeled, either directly or indirectly (e.g., using secondary antibodies, which are typically included in the kit, together with reagents, e.g., buffers, substrates, necessary for their detection). Therapeutic antibodies can be either modified, e.g. by the addition of a cytotoxic agent, or unmodified, working, e.g., by modulating TLR3 activation, or by simply binding to target cells and thereby stimulating or inhibiting them, triggering cell death, or marking them for destruction by the immune system. It will be appreciated that this description of the contents of the kits is not limiting in any way. For example, the kit may contain other types of therapeutic compounds as well, such as other anti-tumor agents. Preferably, the kits also include instructions for using the antibodies, e.g., detailing the herein-described methods.

Further aspects and advantages of this invention will be disclosed in the following experimental section, which should be regarded as illustrative and not limiting the scope of this application.

EXAMPLES

Materials and Methods

Interferon-alpha (IntronA™) was purchased from Schering Plough Corp. Tumor Cell lines: A375 malignant melanoma tumor cell lines (CRL-1619) are purchased from ATCC. Antibodies (antigen, supplier, reference): Anti-TLR3 antibody pAb, R&D Systems, ref. AF1487. Instrumentation: FACSCalibur™ flow cytometer (BD Biosciences).

Inhibition with lentivirus shRNAA lentivirus construction was made and produced by Vectalys (Toulouse, France), encoding short hairpin RNA (shRNA) targeting control human TLR3. Tumor cells were infected with lentivirus preparation and further selected with puromycin to get stable shTLR3A375 tumor cells.

Surface Plasmon resonance (SPR)(a) Biacore T100 general procedure. SPR measurements were performed on a Biacore T100 apparatus (Biacore GE Healthcare) at 25° C. In all Biacore experiments HBS-EP+ buffer (Biacore GE Healthcare) served as running buffer and sensorgrams were analyzed with Biaevaluation 4.1 and Biacore T100 Evaluation software. Recombinant human TLR3 and TLR4 were purchased from R&D Systems.

(b) Protein immobilization. Recombinant TLR3 and TLR4 proteins were immobilized covalently to carboxyl groups in the dextran layer of a Biacore Sensor Chip CM5 (chip). The chip surface was activated with EDC/NHS (0.2M N-ethyl-N'-(3-dimethylaminopropyl) carbodiimidehydrochloride, 0.05M N-hydroxysuccinimide (Biacore GE Healthcare)). Proteins were diluted to 10 µg/ml in coupling buffer (10 mM sodium acetate, pH 5.6) and injected until the appropriate immobilization level was reached (i.e. approximately 2000 RU). Deactivation of the remaining activated groups was performed using 100 mM ethanolamine pH 8 (Biacore GE Healthcare).

(c) Antibody binding analysis. Antibodies at a constant concentration of 10 µg/ml were injected for 2 min at a constant flow rate of 10 µl/min over the immobilized proteins and allowed to dissociate for 3 min before regeneration by a ten second injection of 10 mM NaOH, 500 mM NaCl regeneration buffer. Blank correction is performed on line by co-injecting the soluble antibodies onto the reference dextran flow cell.

Example 1

Comparison with Commercially Available Antibodies

Commercially available anti-TLR3 antibodies were tested in an immunocytochemistry (ICC) assay on 293T and 293-TLR3 cells. Briefly, cells were coated on Marienfeld adhesion slides, (#80107926, VWR) and fixed in cold acetone for 20 nm at 4° C. Cells were permeabilized with permwash (#554723, from BD biosciences) and anti-TLR3 antibodies, labeled with biotin, followed by streptavidine coupled to peroxidase from SIGMA. Staining was revealed with AEC. TLR3.7 antibody yielded faint staining on 293T-TLR3 cells overexpressing TLR3, but no staining on other TLR3 expressing tumor cells. The goat pAb anti-TLR3Ab from R&D systems yielded strong staining on 293T-TLR3, specific since no staining could be obtained on control 293T cells.

The two antibodies were tested in Biacore for binding to immobilized human TLR3 and TLR4 protein. TLR3.7 antibody showed low binding to TLR3 but not TLR4. Likewise, the goat pAb anti TLR3 from R&D systems which showed staining in paraffin-embedded sample, albeit to TLR4 positive samples in addition to TLR3, showed a high response for binding to TLR3 but not TLR4 (see FIG. 1).

Finally several commercially available anti-TLR3 antibodies (reported in their technical datasheet to work mostly in WB assay, but not in FACS or IHC) were tested in a series of assays. The antibodies were tested in an IHC assays for binding to 293T cells, 293T-TLR3 cells and 293T-TLR4 cells, for cells in either frozen cell pellets or in paraffin-embedded cell pellets. Results are shown in Table 1.

TABLE 1

| α h-TLR3 | Supplier | Frozen cell pellet | | | Paraffin-embedded cell pellet | | |
|---|---|---|---|---|---|---|---|
| | | 293T | 293T.T4 | 293T.T3 | 293T | 293T.T4 | 293T.T3 |
| Goat pAb | R&D systems | − | − | + | + | + | + |
| 40C1285.6 | Imgenex | + | + | + | + | + | + |
| TLR3.7 | eBiosciences | − | − | − | − | − | − |
| MCA2267 | Abd Serotec | − | − | − | − | + | + |
| A01 | Abnova | − | − | − | − | − | − |
| Q-18 | Santa Cruz | − | − | − | − | − | − |
| N-14 | Santa Cruz | − | − | + | − | − | − |
| L-13 | Santa Cruz | − | − | − | − | − | − |
| C-20 | Santa Cruz | − | − | + | − | − | − |
| H-125 | Santa Cruz | − | − | − | − | − | − |

In conclusion, although some mAb or pAb are able to detect human TLR3 in ICC, FACS or frozen cell pellet. Among them, only one goat pAb from R&D was able to induce a signal strong enough to stain normal human tissue section with endogenous expression of TLR3 (as opposed to TLR3 overexpressing 293T cells transfected with TLR3). In addition, none of the commercially available antibodies were able to detect human TLR3 in paraffin-embedded cell pellets or tissue section, with specificity for TLR3 over TLR4.

Example 2

Obtaining of TLR3—Specific Monoclonal Antibodies

Primary Screen.

To obtain anti-TLR3 antibodies, Balb/c mice were immunized with a recombinant human His-tagged TLR3 extracellular domain recombinant protein (R&D systems, #1487-TR-050). Mice received one primo-immunisation with an emulsion of 50 µg TLR3 protein and Complete Freund Adjuvant, intraperitoneally, a 2nd immunization with an emulsion of 50 µg TLR3 protein and Incomplete Freund Adjuvant, intraperitoneally, and three boosts with 10 µg TLR3 protein, intravenously. Immune spleen cells were fused with X63.Ag8.653 immortalized B cells, and cultured in the presence of irradiated spleen cells. 40 culture plates were obtained and evaluated in a first screen for TLR3 binding using an ELISA developed for detection of binding to TLR3. Briefly, His-tagged recombinant TLR3 protein (R&D systems, #1487-TR-050) was coated on Ni-NTA 96-wells plates (Qiagen). Supernatant (SN) from hybridoma culture plates and incubated in TLR3-plates, and the presence of TLR3 binding Ig was revealed with goat anti-mouse F(ab) IgG-HRP. Positive supernatants were selected and tested for lack of binding to TLR4. Briefly, His-tagged rec TLR4 protein (R&D systems, #3146-TR-050) were coated on Ni-NTA 96-wells plates (Qiagen). SN from hybridoma culture plates were incubated in TLR4-plates, and the presence of TLR4 binding Ig was revealed with goat anti-mouse F(ab) IgG-HRP. TLR4 was chosen as a $2^{nd}$ screen in order to discriminate among wells selected in the $1^{st}$ screen, where anti-His specific antibody from TLR3 specific antibody were used. Secondly, given the homology between TLR3 and other members of TLR family, the initial assessment in Example 1 demonstrated that at least one commercially available monoclonal antibody (mAb) indicated on its packaging as specific for TLR3 protein nevertheless recognized paraffin-embedded 293T cells stably transfected with TLR4 (Results for available commercial antibodies are shown in Example 1).

Secondary Screen; Selection of Hybridomas of Interest.

168 supernatants were retained and tested in a further screen in a Biacore assay using rec TLR3 chips, followed by various assays formats based on binding to human TLR3-expressing 293T cells. A 293T cell line (ATCC, #CRL-1573), stably transfected with pISRE-luc plasmid (#219089—Stratagene), was further selected as inducing optimal response to IFN-alpha stimulation and referred to as control 293T cells. This cell line was further stably transfected with pUNO-hTLR3 plasmid (#puno-htlr3—InVivogen), or pUNO-hTLR4 plasmid (#puno-tlr4—InVivogen) and referred to respectively as 293T-TLR3 and 293T-TLR4. Supernatants were screened in a FACS based screen for binding to 293T-TLR3 cells with no binding to 293T control cells, and in parallel in an IHC screen for binding to 293T-TLR3 cells as a frozen cell pellet, with no binding to 293T-TLR4 cells. Wells selected in the IHC screen for binding to 293T-TLR3 cells as a frozen cell pellet were also further tested in an IHC screen for binding to 293T-TLR3 cells as a paraffin embedded cell pellet. Briefly, for FACS screening, the presence of reacting antibodies in supernatants were revealed by Goat anti-mouse polyclonal antibody (pAb) labeled with biotin, streptavidin labeled with PE. For IHC screening, presence of reacting antibodies (Abs) in supernatants were revealed by donkey anti-mouse pAb labeled with biotin (#715-065-150, Jackson Immunoresearch Laboratories), streptavidin labeled with peroxydase (#E2886, SIGMA) and revealed with DAB (#SK-4105, Vector Laboratories). Seven supernatants tested positive in this screen for binding to 293T-TLR3 cells in a paraffin embedded cell pellet.

Cloning of Hybridomas of Potential Interest.

42 potentially interesting hybridomas selected from the initial screening were cloned by limiting dilution techniques in 96-wells plates, and 304 subclones were tested in a series of screens as follows. The 304 subclones were first evaluated in a screen for TLR3 binding using the same ELISA developed for detection of binding to TLR3, and positive supernatants were selected and tested for lack of binding to TLR4 in ELISA assay, yielding 228 clones which were selective for TLR3. All supernatants yielding a ratio above 10 for DO obtained in TLR3ELISA to DO obtained in TLR4ELISA were selected as specific for TLR3. Among them was supernatant from well F9 of plate 40 (40F9).

Among the 304 clones, 63 clones, selected as issuing from preclones tested positive in frozen IHC, were also tested in a frozen IHC screen for binding to 293T-TLR3 cells as a frozen cell pellet, with no binding to 293T-TLR4 cells, yielding 31 positive clones in frozen IHC.

Among 71 clones positive in FACS staining and the 31 clones positives in frozen IHC, 60 clones were selected for cryopreservation from the 304 initial clones. These 60 selected clones were also tested in an IHC screen for binding to 293T-TLR3 cells as a paraffin embedded cell pellet and 6 clones were positive for TLR3 binding. Those clones were further tested for binding to human healthy colon tissue embedded in paraffin (#T8235722-5, Biochain), previously reported to be positive for TLR3 expression. Three of them stained positively human colon tissue, all of them issuing for the same pre-clone, 40F9. The clone 40F9.6 yielded the strongest signal and was selected for further TLR3 expression study.

Example 3

Development of an Amplification System and Staining Protocol for 40F9

40F9.6 was tested on tonsil tissue with different detection systems, in order to identify the detection system yielding the strongest signal, with the lowest noise:signal ratio. The ENVISION System commercialized by DAKO A/S (Glostrup, Denmark) was selected. ENVISION is an amplification system based on an HRP-labeled polymer conjugated to secondary antibodies. Tissue sections were dewaxed and rehydrated before the antigen unmasking procedure in boiled citrate buffer (pH6). Endogenous peroxydases were blocked by a 3% solution of $H_2O_2$. 40F9.6, at 10 µg/ml, was applied on tissue sections, incubated for 1 hour at room temperature, and was revealed by using the ENVISION System and DAB-chromogen (Dako, Glostrup, Denmark).

Example 4

Testing Antibodies in Paraffin-Embedded Tissue Sections from Cancer Patients

40F9.6 was tested in a series of paraffin-embedded samples. In a first set of experiments, purified 40F9.6 was tested in an IHC screen for binding to 293T-TLR3 and 293T-TLR4 cells as a paraffin embedded cell pellet from 293T-TLR3 transfectants tissue, at 10 µg/ml, with the amplification protocol described in Example 3. 40F9.6 showed staining on 293T-TLR3 cells but no staining on 293T-TLR4 cells.

In a second set of experiments, purified 40F9.6 was tested in an IHC screen for binding to human A375 melanoma cells treated with interferon-α, in paraffin embedded cell pellet, again at 10 µg/ml, with the amplification protocol described in Example 3. A375 cells were previously identified as TLR3 positive, and interferon-α is reported to additionally enhance TLR3 expression. A control IgG1 antibodies was used for comparison. 40F9 showed staining on A375 cells while control IgG1 showed no staining The same experiment was also carried out in interferon-α treated A375 cells which had been stably infected with a lentiviral construction coding for shRNA targeting TLR3. Staining by 40F9.6 but not IgG1 decreased substantially in the A375 cells treated with shRNA.

In a further set of experiments, purified 40F9.6 was tested in an IHC screen for binding to various healthy human tissue in paraffin embedded tissue sections, again at 10 µg/ml, with the amplification protocol described in Example 3, using control IgG1 antibodies was used for comparison. 40F9.6 but not IgG1 showed staining in breast, tonsil, esophagus, skin, cerebellum and pancreas tissue. The same experiment was repeated in a series of healthy human tissues using antibody PolyR&D (R&D Systems), which has been reported to bind human TLR3. Both 40F9.6 and PolyR&D antibodies stained skin, cerebellum, breast, lung, esophagus, stomach, ileum, jejunum, duodenum, colon, liver, pancreas, testis, spleen, thymus thyroid and kidney.

In another set of experiments, 40F9.6 was tested in an IHC screen for binding to various human tumor tissues in paraffin embedded tissue sections, a standard donkey anti-mouse biotin amplification, instead of the Envison™ system. 10 tumor samples were used for each tumor indication. 40F9.6 showed strong staining in several tumor types, including lung (6 of 10 samples), esophagus (8 of 10 samples), stomach (4 of 10 samples), larynx (4 of 10 samples) and cervix (7 of 10 samples).

In another set of experiments, purified 40F9.6 was tested in an IHC screen for binding to melanoma tissue samples in paraffin embedded tissue sections from 9 human patients. Melanomas were generally from patients who either did or did not receive interferon-α treatment prior to biopsy. 40F9.6 was used at 10 µg/ml, using both the standard biotine amplification and Envision™ amplification systems. 40F9.6 showed staining in 8 or 9 patients, ranging in degree of staining, and staining in patients both who received or did not undergo interferon-α treatment. The patients not treated with interferon-α represented three of the eight patients; one of these non-treated patients showed strong staining with 40F9.6, one showed no staining and one showed a low level of staining.

In these experiments, 40F9.6 clone appears to stain specifically TLR3 in a great variety of paraffin embedded tissues, with a selectivity higher than any of the currently available TLR3 antibodies.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of" "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law. All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. A method of treating a cancer patient, said method comprising:
   a) providing a paraffin-embedded tissue section of cancerous tissue from a patient having melanoma breast cancer, lung cancer, esophageal cancer, stomach cancer, cancer of the larynx, kidney cancer or cervical cancer and detecting TLR3 in said paraffin-embedded cancerous tissue section with a monoclonal antibody that specifically binds to TLR3 in paraffin-embedded cancerous tissue sections, said monoclonal antibody comprising:
      i) variable light chain region CDRs: KSSQSLLDS-DGKTYLN (SEQ ID NO:5; CDR1); LVSKLDS (SEQ ID NO:6; CDR2); and WQGIHLPYT (SEQ ID NO:7; CDR3) and variable heavy chain region CDRs: YTFTNYGMN (SEQ ID NO:8; CDR1); NANT-GEPTYAEEFKG (SEQ ID NO:9; CDR2); and DYDY (SEQ ID NO:10; CDR3); or
      ii) variable light chain region CDRs: KSSQSLLDS-DGKTYLN (SEQ ID NO:5; CDR1); LVSKLDS (SEQ ID NO:6; CDR2); and WQGIHLPYT (SEQ ID NO:7; CDR3) and variable heavy chain region CDRs: KASGYTFTNYGMN (SEQ ID NO:11; CDR1); NANTGEPTYAEEFKG (SEQ ID NO:9; CDR2); and DYDY (SEQ ID NO:10; CDR3); and
   b) treating a cancer patient positive for the presence of TLR3 in said paraffin-embedded cancerous tissue section by administering a TLR3 ligand to said cancer patient.

2. The method of claim 1, wherein the TLR3 ligand is selected from the group consisting of a dsRNA, polyIC, polyAU, an activating anti-TLR3 antibody and an agent capable of inducing apoptosis of TLR3-expressing cells.

3. The method of claim 1, wherein said paraffin-embedded cancerous tissue section contains breast cancer tissue.

4. The method of claim 1, wherein said paraffin-embedded cancerous tissue section contains lung cancer tissue.

5. The method of claim 1, wherein said paraffin-embedded cancerous tissue section contains esophageal cancer tissue.

6. The method of claim 1, wherein said paraffin-embedded cancerous tissue section contains stomach cancer tissue.

7. The method of claim 1, wherein said paraffin-embedded cancerous tissue section contains larynx cancer tissue.

8. The method of claim 1, wherein said paraffin-embedded cancerous tissue section contains kidney cancer tissue.

9. The method of claim 1, wherein said paraffin-embedded cancerous tissue section contains cervical cancer tissue.

10. The method of claim 1, wherein said paraffin-embedded cancerous tissue section contains melanoma tissue.

* * * * *

UNITED STATES PATENT AND TRADEMARK OFFICE
CERTIFICATE OF CORRECTION

PATENT NO. : 8,715,667 B2
APPLICATION NO. : 13/585874
DATED : May 6, 2014
INVENTOR(S) : Karine Chemin et al.

Page 1 of 1

It is certified that error appears in the above-identified patent and that said Letters Patent is hereby corrected as shown below:

In the Specification

Column 9,
Line 34, "CNCM 1-4061." should read --CNCM I-4061.--.

Column 29,
Line 33, "may between" should read --may be between--.

Column 32,
Line 27, "shTLR3A375" should read --shTLR3 A375--.

Column 33,
Line 5, "anti-TLR3Ab" should read --anti-TLR3 Ab--.
Line 66, "20 nm" should read --20mn- --.

Column 35,
Line 11, "TLR3ELISA" should read --TLR3 ELISA--.
Line 11, "TLR4ELISA" should read --TLR4 ELISA--.

In the Claims

Column 49,
Line 53, "melanoma breast" should read --melanoma, breast--.

Signed and Sealed this
Twenty-first Day of October, 2014

Michelle K. Lee
*Deputy Director of the United States Patent and Trademark Office*